United States Patent
Zhu

(10) Patent No.: US 9,944,928 B2
(45) Date of Patent: Apr. 17, 2018

(54) CONSTRUCTION OF POOL OF INTERFERING NUCLEIC ACIDS COVERING ENTIRE RNA TARGET SEQUENCE AND RELATED COMPOSITIONS

(71) Applicant: York Yuan Yuan Zhu, Palo Alto, CA (US)

(72) Inventor: York Yuan Yuan Zhu, Palo Alto, CA (US)

(73) Assignee: York Yuan Yuan Zhu, Palo Alto, CA (US)

(*) Notice: Subject to any disclaimer, the term of this patent is extended or adjusted under 35 U.S.C. 154(b) by 0 days.

(21) Appl. No.: 14/791,157

(22) Filed: Jul. 2, 2015

(65) Prior Publication Data

US 2015/0299707 A1 Oct. 22, 2015

Related U.S. Application Data

(63) Continuation of application No. 12/313,554, which is a continuation of application No. PCT/CN2008/001283, filed on Jul. 7, 2008, now abandoned.

(30) Foreign Application Priority Data

Jul. 23, 2007 (CN) .......................... 2007 1 0024217

(51) Int. Cl.
| | |
|---|---|
| C12N 15/11 | (2006.01) |
| C12N 15/113 | (2010.01) |
| C40B 40/08 | (2006.01) |
| C40B 50/06 | (2006.01) |

(52) U.S. Cl.
CPC .......... *C12N 15/113* (2013.01); *C12N 15/111* (2013.01); *C40B 40/08* (2013.01); *C40B 50/06* (2013.01); *C12N 2310/14* (2013.01); *C12N 2330/31* (2013.01)

(58) Field of Classification Search
CPC . C12N 15/111; C12N 15/113; C12N 15/1093; C12N 15/66; C12N 2310/14
See application file for complete search history.

(56) References Cited

U.S. PATENT DOCUMENTS

| | | |
|---|---|---|
| 2005/0233994 A1 | 10/2005 | Kaykas et al. |
| 2006/0024681 A1 | 2/2006 | Smith et al. |
| 2007/0270360 A1* | 11/2007 | McSwiggen ....... C12N 15/1131 514/44 A |
| 2008/0008993 A1 | 1/2008 | Kahl et al. |
| 2008/0021205 A1 | 1/2008 | Blau |
| 2009/0099043 A1 | 4/2009 | Zhu |
| 2009/0111705 A1 | 4/2009 | Sparks et al. |

FOREIGN PATENT DOCUMENTS

| | | |
|---|---|---|
| CN | 101113456 | 1/2008 |
| CN | 101126176 | 2/2008 |
| WO | 2004085608 | 10/2004 |

OTHER PUBLICATIONS

Taki et al., Small-interfering RNA expression in cells based on an efficiently constructed dumbbell-shaped DNA, 2004, Angewandte Chemie International Edition, vol. 43, pp. 3160-3163.*
Du et al., Generation of variable and fixed length siRNA from a novel siRNA expression vector, 2006, Biochemical and Biophysical Research Communications, vol. 345, pp. 99-105.
Seyhan et al., Complete, gene-specific siRNA libraries: Production and expression in mammalian cells, 2005, RNA, vol. 11, pp. 837-846.
Matsumura et al., Gene expression analysis of plant host-pathogen interactions by Super SAGE, 2003, PNAS, vol. 100, pp. 15718-15723.
Catto et al., Protein assembly and DNA looping by the FokI restriction endonuclease, 2006, Nucleic Acids Research, vol. 34, pp. 1711-1720.
Mucke et al. DNA cleavage by type III restriction-modification enzyme EcoP15I is independent of spacer distance between two head to head oriented recognition sites, 2001, JMB, vol. 312, pp. 687-698.
Kaykas et al., A plasmid-based system for expressing small interfering RNA libraries in mammalian cells, 2004, BMC Cell Biology, vol. 5:16, pp. 1-11.
Dinh et al., Alternative approach to generate shRNA from eDNA, 2005, BioTechniques, vol. 38, pp. 629-632.
Restriction enzyme MmeI, New England Biolabs product instruction, accessed and retrieved from www.neb.com on Feb. 6, 2014.

* cited by examiner

*Primary Examiner* — Dana H Shin
(74) *Attorney, Agent, or Firm* — K&L Gates LLP; Louis C. Cullman; David Diamond

(57) ABSTRACT

The present invention provides a PCR based high-throughput method for preparing full-sites siRNA polynucleotide pool, comprising: DNase I random digestion; Loop-1 phosphate linker ligation; single PCR amplification; a type III restriction/modification enzyme digestion; blunt ending; Loop-2 phosphate linker ligation; double primer PCR; FokI digestion and cloning into an siRNA expression vector. The present invention enables the use of a type III restriction/modification enzyme linkers mediated PCR method for high-throughput preparing an siRINA polynucleotide pool, in which the functional length of siRNAs can be controllably distributed from 19-23 bp, thus completely mimic the natural siRNA length diversity, specially suitable for RNAi therapeutic targets screening. The present invention overcomes the bottlenecks and drawbacks of conventional siRNA polynucleotide pool construction technologies.

16 Claims, 2 Drawing Sheets

1.) DNase I partially digested DNA and Loop-1 mixture ligation:

2.) Single primer PCR:

3.) EcoP15 I digestion:

(19-23bp)    (19-23bp)

4.) End polishing and Loop-2 ligation:

(19-23bp)    (Loop-2)

5.) 5' & 3' PCR:

6.) Fok I digestion:

(19-23bp)

7.) Cloning to an siRNA expression

SEQUENCE LISTING

<160> NUMBER OF SEQ ID NOS: 80

<210> SEQ ID NO 1
<211> LENGTH: 6
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n = any nucleotide

```
<400> SEQUENCE: 1 cagcan                                                                6

<210> SEQ ID NO 2
<211> LENGTH: 7
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n = any nucleotide

<400> SEQUENCE: 2 ngtgctg                                                               7

<210> SEQ ID NO 3
<211> LENGTH: 6
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n = any nucleotide

<400> SEQUENCE: 3 ntgctg                                                                6

<210> SEQ ID NO 4
<211> LENGTH: 7
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n = any nucleotide

<400> SEQUENCE: 4 cagcacn                                                               7

<210> SEQ ID NO 5
<211> LENGTH: 6
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n = any nucleotide

<400> SEQUENCE: 5 cttttn                                                                6

<210> SEQ ID NO 6
<211> LENGTH: 6
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n = any  nucleotide

<400> SEQUENCE: 6 gaaaan                                                                6

<210> SEQ ID NO 7
<211> LENGTH: 5
<212> TYPE: DNA
<213> ORGANISM: Escherichia coli
```

<400> SEQUENCE: 7 aaaaa                                                                    5

<210> SEQ ID NO 8
<211> LENGTH: 5
<212> TYPE: DNA
<213> ORGANISM: Escherichia coli

<400> SEQUENCE: 8 ttttt                                                                    5

<210> SEQ ID NO 9
<211> LENGTH: 7
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n = any nucleotide

<400> SEQUENCE: 9 gtcgtcn                                                                  7

<210> SEQ ID NO 10
<211> LENGTH: 7
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n = any nucleotide

<400> SEQUENCE: 10 nctgctg                                                                  7

<210> SEQ ID NO 11
<211> LENGTH: 7
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n = any nucleotide

<400> SEQUENCE: 11 ngacgac                                                                  7

<210> SEQ ID NO 12
<211> LENGTH: 7
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n = any nucleotide

<400> SEQUENCE: 12 cagcagn                                                                  7

<210> SEQ ID NO 13
<211> LENGTH: 7
<212> TYPE: DNA
<213> ORGANISM: Escherichia coli
<220> FEATURE:
<221> NAME/KEY: misc_feature
<222> LOCATION: (1)..(1)

```
<223> OTHER INFORMATION: n = any nucleotide

<400> SEQUENCE: 13 ngacgac                                                                    7

<210> SEQ ID NO 14
<211> LENGTH: 7
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n = any nucleotide

<400> SEQUENCE: 14 nctgctg                                                                    7

<210> SEQ ID NO 15
<211> LENGTH: 7
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n = any nucleotide

<400> SEQUENCE: 15 ctcgtcn                                                                    7

<210> SEQ ID NO 16
<211> LENGTH: 7
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n = any nucleotide

<400> SEQUENCE: 16 cagcagn                                                                    7

<210> SEQ ID NO 17
<211> LENGTH: 6
<212> TYPE: DNA
<213> ORGANISM: Escherichia coli

<400> SEQUENCE: 17 cagcag                                                                     6

<210> SEQ ID NO 18
<211> LENGTH: 5
<212> TYPE: DNA
<213> ORGANISM: Escherichia coli

<400> SEQUENCE: 18 ggatg                                                                      5

<210> SEQ ID NO 19
<211> LENGTH: 5
<212> TYPE: DNA
<213> ORGANISM: Escherichia coli

<400> SEQUENCE: 19 gtagg                                                                      5
```

```
<210> SEQ ID NO 20
<211> LENGTH: 5
<212> TYPE: DNA
<213> ORGANISM: Escherichia coli

<400> SEQUENCE: 20 catcc                                                                     5

<210> SEQ ID NO 21
<211> LENGTH: 5
<212> TYPE: DNA
<213> ORGANISM: Escherichia coli

<400> SEQUENCE: 21 cctac                                                                     5

<210> SEQ ID NO 22
<211> LENGTH: 5
<212> TYPE: DNA
<213> ORGANISM: Escherichia coli

<400> SEQUENCE: 22 cctac                                                                     5

<210> SEQ ID NO 23
<211> LENGTH: 5
<212> TYPE: DNA
<213> ORGANISM: Escherichia coli

<400> SEQUENCE: 23 ggatg                                                                     5

<210> SEQ ID NO 24
<211> LENGTH: 4
<212> TYPE: DNA
<213> ORGANISM: Escherichia coli

<400> SEQUENCE: 24 aaaa                                                                      4

<210> SEQ ID NO 25
<211> LENGTH: 44
<212> TYPE: DNA
<213> ORGANISM: Escherichia coli

<400> SEQUENCE: 25
ctttttttct gctgcatccc tgaactggga tccgttggat gtgt                          44

<210> SEQ ID NO 26
<211> LENGTH: 44
<212> TYPE: DNA
<213> ORGANISM: Escherichia coli

<400> SEQUENCE: 26
acacatccaa cggatcccag ttcagggatg cagcagaaaa aaag                          44

<210> SEQ ID NO 27
<211> LENGTH: 44
<212> TYPE: DNA
<213> ORGANISM: Escherichia coli

<400> SEQUENCE: 27
cttttttctg ctggcatccc tgaactggga tccgttggat gtgt                          44
```

<210> SEQ ID NO 28
<211> LENGTH: 44
<212> TYPE: DNA
<213> ORGANISM: Escherichia coli

<400> SEQUENCE: 28
acacatccaa cggatcccag ttcagggatg ccagcagaaa aaag         44

<210> SEQ ID NO 29
<211> LENGTH: 44
<212> TYPE: DNA
<213> ORGANISM: Escherichia coli

<400> SEQUENCE: 29 cttttctgc tgggcatccc tgaactggga tccgttggat gtgt          44

<210> SEQ ID NO 30
<211> LENGTH: 44
<212> TYPE: DNA
<213> ORGANISM: Escherichia coli

<400> SEQUENCE: 30
acacatccaa cggatcccag ttcagggatg cccagcagaa aaag         44

<210> SEQ ID NO 31
<211> LENGTH: 44
<212> TYPE: DNA
<213> ORGANISM: Escherichia coli

<400> SEQUENCE: 31
cttttctgct ggggcatccc tgaactggga tccgttggat gtgt         44

<210> SEQ ID NO 32
<211> LENGTH: 44
<212> TYPE: DNA
<213> ORGANISM: Escherichia coli

<400> SEQUENCE: 32
acacatccaa cggatcccag ttcagggatg ccccagcaga aaag         44

<210> SEQ ID NO 33
<211> LENGTH: 44
<212> TYPE: DNA
<213> ORGANISM: Escherichia coli

<400> SEQUENCE: 33
ttttctgctg ggggcatccc tgaactggga tccgttggat gtgt         44

<210> SEQ ID NO 34
<211> LENGTH: 44
<212> TYPE: DNA
<213> ORGANISM: Escherichia coli

<400> SEQUENCE: 34
acacatccaa cggatcccag ttcagggatg cccccagcag aaaa         44

<210> SEQ ID NO 35
<211> LENGTH: 45
<212> TYPE: DNA
<213> ORGANISM: Escherichia coli

<400> SEQUENCE: 35 cttttttgaga ccgacatccc tctgcagacg atccatcaga gtcag       45

<210> SEQ ID NO 36
<211> LENGTH: 45
<212> TYPE: DNA
<213> ORGANISM: Escherichia coli

<400> SEQUENCE: 36
ctgactctga tggatcgtct gcagagggat gtcggtctca aaaag         45

<210> SEQ ID NO 37
<211> LENGTH: 25
<212> TYPE: DNA
<213> ORGANISM: Escherichia coli

<400> SEQUENCE: 37
acacatccaa cggatcccag ttcag         25

<210> SEQ ID NO 38
<211> LENGTH: 25
<212> TYPE: DNA
<213> ORGANISM: Escherichia coli

<400> SEQUENCE: 38
acacatccaa cggatcccag ttcag         25

<210> SEQ ID NO 39
<211> LENGTH: 24
<212> TYPE: DNA
<213> ORGANISM: Escherichia coli

<400> SEQUENCE: 39
gactctgatg gatcgtctgc agag         24

<210> SEQ ID NO 40
<211> LENGTH: 21
<212> TYPE: DNA
<213> ORGANISM: Escherichia coli

<400> SEQUENCE: 40
aaggtcgggc aggaagaggg c         21

<210> SEQ ID NO 41
<211> LENGTH: 24
<212> TYPE: DNA
<213> ORGANISM: Escherichia coli

<400> SEQUENCE: 41
tatttgcatg tcgctatgtg ttct         24

<210> SEQ ID NO 42
<211> LENGTH: 5
<212> TYPE: DNA
<213> ORGANISM: Escherichia coli

<400> SEQUENCE: 42 aaaag         5

<210> SEQ ID NO 43
<211> LENGTH: 21
<212> TYPE: DNA
<213> ORGANISM: SARS coronavirus

<400> SEQUENCE: 43

```
tacaatttgc ctattctaat c                                         21

<210> SEQ ID NO 44
<211> LENGTH: 20
<212> TYPE: DNA
<213> ORGANISM: SARS coronavirus

<400> SEQUENCE: 44
ggctcttgtg gccagtaaca                                           20

<210> SEQ ID NO 45
<211> LENGTH: 20
<212> TYPE: DNA
<213> ORGANISM: SARS coronavirus

<400> SEQUENCE: 45
ggaaaacaag ctttattatg                                           20

<210> SEQ ID NO 46
<211> LENGTH: 19
<212> TYPE: DNA
<213> ORGANISM: SARS coronavirus

<400> SEQUENCE: 46
tacggtagcg gttgtatgc                                            19

<210> SEQ ID NO 47
<211> LENGTH: 20
<212> TYPE: DNA
<213> ORGANISM: SARS coronavirus

<400> SEQUENCE: 47
tattctaatc ggaacaggtt                                           20

<210> SEQ ID NO 48
<211> LENGTH: 22
<212> TYPE: DNA
<213> ORGANISM: SARS coronavirus

<400> SEQUENCE: 48
gagcaaacag cctgaaggaa gc                                        22

<210> SEQ ID NO 49
<211> LENGTH: 20
<212> TYPE: DNA
<213> ORGANISM: SARS coronavirus

<400> SEQUENCE: 49
gtacccgctc aatgtggtca                                           20

<210> SEQ ID NO 50
<211> LENGTH: 23
<212> TYPE: DNA
<213> ORGANISM: SARS coronavirus

<400> SEQUENCE: 50
gtacataata aagcttgttt tcc                                       23

<210> SEQ ID NO 51
<211> LENGTH: 19
<212> TYPE: DNA
<213> ORGANISM: SARS coronavirus

<400> SEQUENCE: 51
```

-continued agaatgtttg tttctgggt                                                  19

<210> SEQ ID NO 52
<211> LENGTH: 20
<212> TYPE: DNA
<213> ORGANISM: SARS coronavirus

<400> SEQUENCE: 52
cattggtgct gtgatcattc                                                 20

<210> SEQ ID NO 53
<211> LENGTH: 20
<212> TYPE: DNA
<213> ORGANISM: SARS coronavirus

<400> SEQUENCE: 53
gagaatgttt gtttctgggt                                                 20

<210> SEQ ID NO 54
<211> LENGTH: 20
<212> TYPE: DNA
<213> ORGANISM: SARS coronavirus

<400> SEQUENCE: 54
ctttattatg tacaaaaacc                                                 20

<210> SEQ ID NO 55
<211> LENGTH: 20
<212> TYPE: DNA
<213> ORGANISM: SARS coronavirus

<400> SEQUENCE: 55
gattagaata ggcaaattgt                                                 20

<210> SEQ ID NO 56
<211> LENGTH: 23
<212> TYPE: DNA
<213> ORGANISM: SARS coronavirus

<400> SEQUENCE: 56
ggaagcaacg aagtagctaa gcc                                             23

<210> SEQ ID NO 57
<211> LENGTH: 22
<212> TYPE: DNA
<213> ORGANISM: SARS coronavirus

<400> SEQUENCE: 57
gagcgggtac gagcaaacag cc                                              22

<210> SEQ ID NO 58
<211> LENGTH: 21
<212> TYPE: DNA
<213> ORGANISM: SARS coronavirus

<400> SEQUENCE: 58
tctccggggg acaattgtga c                                               21

<210> SEQ ID NO 59
<211> LENGTH: 22
<212> TYPE: DNA
<213> ORGANISM: SARS coronavirus

```
<400> SEQUENCE: 59
tgttactaca atttgcctat tc                                          22

<210> SEQ ID NO 60
<211> LENGTH: 21
<212> TYPE: DNA
<213> ORGANISM: SARS coronavirus

<400> SEQUENCE: 60
gctttattat gtacaaaaac c                                           21

<210> SEQ ID NO 61
<211> LENGTH: 21
<212> TYPE: DNA
<213> ORGANISM: SARS coronavirus

<400> SEQUENCE: 61
gaatgaccac attgagcggg t                                           21

<210> SEQ ID NO 62
<211> LENGTH: 20
<212> TYPE: DNA
<213> ORGANISM: SARS coronavirus

<400> SEQUENCE: 62
gtgatgtagc cacagtgatc                                             20

<210> SEQ ID NO 63
<211> LENGTH: 21
<212> TYPE: DNA
<213> ORGANISM: SARS coronavirus

<400> SEQUENCE: 63
tcaacccaga aacaaacatt c                                           21

<210> SEQ ID NO 64
<211> LENGTH: 22
<212> TYPE: DNA
<213> ORGANISM: SARS coronavirus

<400> SEQUENCE: 64
gtattgtagg cttgatgtgg ct                                          22

<210> SEQ ID NO 65
<211> LENGTH: 22
<212> TYPE: DNA
<213> ORGANISM: SARS coronavirus

<400> SEQUENCE: 65
ctacaatttg cctattctaa tc                                          22

<210> SEQ ID NO 66
<211> LENGTH: 22
<212> TYPE: DNA
<213> ORGANISM: SARS coronavirus

<400> SEQUENCE: 66
tacaatacaa gccattgcaa tc                                          22

<210> SEQ ID NO 67
<211> LENGTH: 22
<212> TYPE: DNA
<213> ORGANISM: SARS coronavirus
```

```
<400> SEQUENCE: 67
catcaagcct acaatacaag cc                                              22

<210> SEQ ID NO 68
<211> LENGTH: 6
<212> TYPE: DNA
<213> ORGANISM: Unknown
<220> FEATURE:
<223> OTHER INFORMATION: Bacteria

<400> SEQUENCE: 68 gtaatg                                                                 6

<210> SEQ ID NO 69
<211> LENGTH: 6
<212> TYPE: DNA
<213> ORGANISM: Unknown
<220> FEATURE:
<223> OTHER INFORMATION: Bacteria

<400> SEQUENCE: 69 gtatac                                                                 6

<210> SEQ ID NO 70
<211> LENGTH: 6
<212> TYPE: DNA
<213> ORGANISM: Escherichia coli

<400> SEQUENCE: 70 catatg                                                                 6

<210> SEQ ID NO 71
<211> LENGTH: 19
<212> TYPE: DNA
<213> ORGANISM: Escherichia coli
<220> FEATURE:
<221> NAME/KEY: misc_feature
<222> LOCATION: (14)..(14)
<223> OTHER INFORMATION: n = any nucleotide

<400> SEQUENCE: 71
cttttttctg ctgncatcc                                                  19

<210> SEQ ID NO 72
<211> LENGTH: 19
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n = any nucleotide

<400> SEQUENCE: 72
ggatgncagc agaaaaaag                                                  19

<210> SEQ ID NO 73
<211> LENGTH: 19
<212> TYPE: DNA
<213> ORGANISM: Escherichia coli
<220> FEATURE:
<221> NAME/KEY: misc_feature
<222> LOCATION: (13)..(14)
<223> OTHER INFORMATION: n = any nucleotide

<400> SEQUENCE: 73
```

```
cttttctgc tgnncatcc                                              19
```

<210> SEQ ID NO 74
<211> LENGTH: 19
<212> TYPE: DNA
<213> ORGANISM: Escherichia coli
<220> FEATURE:
<221> NAME/KEY: misc_feature
<222> LOCATION: (6)..(7)
<223> OTHER INFORMATION: n = any nucleotide

<400> SEQUENCE: 74

```
ggatgnncag cagaaaaag                                             19
```

<210> SEQ ID NO 75
<211> LENGTH: 19
<212> TYPE: DNA
<213> ORGANISM: Escherichia coli
<220> FEATURE:
<221> NAME/KEY: misc_feature
<222> LOCATION: (12)..(14)
<223> OTHER INFORMATION: n = any nucleotide

<400> SEQUENCE: 75

```
cttttctgct gnnncatcc                                             19
```

<210> SEQ ID NO 76
<211> LENGTH: 19
<212> TYPE: DNA
<213> ORGANISM: Escherichia coli
<220> FEATURE:
<221> NAME/KEY: misc_feature
<222> LOCATION: (6)..(8)
<223> OTHER INFORMATION: n = any nucleotide

<400> SEQUENCE: 76

```
ggatgnnnca gcagaaaag                                             19
```

<210> SEQ ID NO 77
<211> LENGTH: 19
<212> TYPE: DNA
<213> ORGANISM: Escherichia coli
<220> FEATURE:
<221> NAME/KEY: misc_feature
<222> LOCATION: (11)..(14)
<223> OTHER INFORMATION: n = any nucleotide

<400> SEQUENCE: 77

```
ttttctgctg nnnncatcc                                             19
```

<210> SEQ ID NO 78
<211> LENGTH: 19
<212> TYPE: DNA
<213> ORGANISM: Escherichia coli
<220> FEATURE:
<221> NAME/KEY: misc_feature
<222> LOCATION: (6)..(9)
<223> OTHER INFORMATION: n = any nucleotide

<400> SEQUENCE: 78

```
ggatgnnnnc agcagaaaa                                             19
```

<210> SEQ ID NO 79
<211> LENGTH: 19
<212> TYPE: DNA
<213> ORGANISM: Escherichia coli

<400> SEQUENCE: 79

```
cttttttct gctgcatcc                                                        19

<210> SEQ ID NO 80
<211> LENGTH: 19
<212> TYPE: DNA
<213> ORGANISM: Escherichia coli

<400> SEQUENCE: 80
ggatgcagca gaaaaaaag                                                       19
```

US 9,944,928 B2

CONSTRUCTION OF POOL OF INTERFERING NUCLEIC ACIDS COVERING ENTIRE RNA TARGET SEQUENCE AND RELATED COMPOSITIONS

CROSS REFERENCE TO RELATED APPLICATIONS

This application is a continuation of U.S. patent application Ser. No. 12/313,554, filed Nov. 21, 2008, which claims priority to International Patent Application PCT/CN2008/001283 filed on Jul. 7, 2008, which claims priority to Chinese Patent Application 200710024217.6, filed on Jul. 23, 2007, the entire contents of all of which are incorporated by reference herein.

FIELD

The present invention relates to methods and compositions for constructing a pool of interfering nucleic acids (iNA) from a sample and the selected polynucleotide pools produced thereby, more particularly for preparing an NA polynucleotide pool using type III restriction/modification enzymes and the corresponding linkers.

BACKGROUND

The teachings of all of the references cited herein are incorporated in their entirety by reference. An understanding of the biological role of any gene comes only after observing the phenotypic consequences of altering the function of that gene in a living cell or organism. RNA interference (RNAi) is a well-established experimental technology for silencing gene expression both in cultured eukaryotic cells and living organisms. RNAi also be used as gene therapy for treating viral infections, cancer, vascular diseases and other diseases in which the down-regulation of a polypeptide would ameliorate the disease. RNAi induces the sequence-specific degradation of a single mRNA species by short interfering RNA (siRNA, a double-stranded small interference RNA), which is believed to be processed through the highly conserved Dicer family of RNase III enzymes in vivo. The process includes: 1) the delivery of homologous double-stranded RNAs (dsRNAs) to the cytoplasm of a cell. 2) dsRNA cleavage by the RNase III-like enzyme, Dicer, to 21~23 bp siRNAs. 3) siRNA incorporation into a protein complex, the RNA-induced silence complex (RISC). 4) the antisense strand of the duplex siRNA guiding the RISC to the homologous mRNA, where the RISC-associated endoribonuclease cleaves the target mRNA, resulting in silencing of the target gene.

As used herein a siRNA is also an interfering nucleic acid (iNA) as some of these interfering nucleic acids may contain a deoxyribonucleic acid placed in the iNA to inhibit RNA nucleases. The siRNA molecule of interest can be synthesized in vitro by chemical and enzymatic (fur example by using the enzyme Dicer) methods. They can also be synthesized in vivo. When a synthetic oligonucleotide is cloned into siRNA expression vectors with a RNA polymerase III promoter (including U6, human H1, and tRNA promoters), or a polymerase II promoter with a minimal poly(A) signal sequence, siRNA can be transcribed in vivo. Typically a single promoter is used to express a short hairpin (shRNA) sequence, although two tandem polymerase III promoters have also been used to transcribe the sense and antisense siRNA sequences. In addition to plasmid-based systems, PCR-derived siRNA expression cassettes based on the single-promoter system is an alternative format for suppressing transfected gene activity.

The siRNA-mediated gene silencing efficiency is affected by many parameters. An important limiting fact is that only about 25% of selected target siRNA sequences are functional due to some factors, such as secondary structures, non-gene-specific reactions and other unknown factors. Thus several synthetic siRNAs need to be generated and tested for every target gene. Thus, it is very expensive and time consuming to identify a suitable iNA construct. Another difficulty is the fact that an iNA sequence may have enough complementarity to the sequence of a second, unintended RNA. This is called the so-called off-target effect. Furthermore, to find the best siRNA binding sites (RNAi drug targets) is very challenging. To resolve the off-target phenomenon, extensive studies have been done on selecting specific target sequences for siRNA. Using algorithms based on sequence-efficacy correlations is the current practice for designing effective siRNAs. Although these criteria significantly increase chance of success for achieving gene silencing, there are many highly effective siRNA sequences that are not determined by the current algorithms because different genes have different sequence preferences. To ensure that the best iNAs are identified, an siRNA library constructed from cDNA or DNA offers a better alternative way to search for sequences that have the best potential silencing effect. Moreover, such an siRNA library can be a useful research tool in functional genomics, and useful for screening RNAi therapeutic targets in a high-throughput manner.

Recently siRNA library approaches (such as whole genomic or gene-specific or domain-specific siRNA libraries) have become a powerful tool for screening RNAi therapeutic targets. In all those approaches, efforts to generate siRNA sequences having an appropriate length have used MmeI-a type II restriction enzyme, by which a maximum 20 nucleotides can be generated. However, a siRNA having a maximum length of 20 bp cannot completely mimic the cleavage product, having a length of 21-23 bp produced by an RNase III-like enzyme-Dicer. This can result in the best siRNA target sites being underrepresented. In all these approaches, the doable-stranded (ds) cDNA is randomly cleaved into small fragments by DNase I (some use restriction enzymes for fragmentation but the representation is an issue) and subsequently ligated to an artificial loop-anchor which contains a MmeI-type II restriction site, then digested by the MmeI restriction enzyme to cut 18-20 nucleotides away from the recognized site. Through complex and multiple process steps including a second anchor ligation, loop extension and PAGE purifications, the ds-cDNA is then converted into a 20-nt palindromic structure with a loop (shRNA) and finally cloned into an siRNA expression vector with an RNA polymerase III promoter. In all these approaches, efforts to generate siRNA sequences having an appropriate length have used a MmeI restriction enzyme, by which only an iNA having a maximum 20 nucleotides can be generated. This is the longest iNA that can be generated using the type II restriction enzymes.

However, there are a number drawbacks in this approach include the following: 1) An shRNA library cannot be generated by PCR due to a palindromic structure. The complicated steps together with heavy cDNA loss in multiple process steps make this approach difficult and impossible to be developed into a high-throughput tool for functional genomics and for siRNA therapeutic target screening. 2) A palindromic structure is unstable during cloning in *E. coli*. This can lead to reduction in library complexity and potential loss of the best therapeutic target sites. 3) An iNA having a maximum of 20 bp cannot completely mimic the cleavage products having 21 to 23 bp produced by an RNase III enzyme like Dicer.

An attempt to construct a siRNA library from cDNA using PCR has currently been reported. In this system, the dsRNAs corresponding to the cDNA of interest are prepared by T7 RNA polymerase mediated transcription from DNA templates flanked by a T7 RNA promoter and subsequent annealing. The dsRNAs are then digested with cloned human Dicer in vitro, yielding 21~23 bp siRNAs. A modified bacterial RNase III can be used to replace Dicer, but the generated siRNA is 20~25 bp. Cleavage products are denatured, purified by PAGE and dephosphorylated. RNA adapters are attached subsequently to the 3'- and 5'-ends of the cleavage products by T4 RNA ligase. RNAs are subsequently converted into dsDNA by RT-PCR using primers complementary to the adapters. After digestion with appropriate restriction enzymes, the 21~23 bp siRNAs corresponding to the cDNA fragments are ligated into an siRNA expression vector having the dual RNA polymerase III promoters, U6 and H1. For a description of the U6 and H1 promoters see US patent application publication no. 20050064489. Taking advantage of PCR, this approach can tolerate the a heavy loss of starting material due to multiple process steps and still generate enough molecules for cloning. Another advantage is that by using RNA fragmentation with Dicer, a distinct random pools of iNAs having 21~23 bp in length can be generated. However, the cDNA-RNA-cDNA conversion process steps are obviously a complex, and even more complicated than shRNA library construction described above. Furthermore, RNA degradation during multiple process steps (e.g., T7 DNA polymerase-mediated DNA to RNA transcription, Dicer digestion, RNA PAGE purification, dephosphate and anchor ligation as well as RT-PCR) is unavoidable, which may result in the loss of some of the best siRNA target sites.

Another attempt at siRNA library construction is based on DNase I digestion. In this approach, dscDNA is partially digested with DNase I, followed by PAGE gel purification isolating DNA fragments that are 20-30 bp in lengths. These fragments are either directly blunt-end cloned into siRNA expression vector or attached to a PCR anchor by ligation, followed by PCR amplification and subsequently cloning into siRNA expression vector. It sounds much simpler and straightforward. However, cutting a nucleic acid fragment that is 20~30 bp length from a PAGE gel is very challenging. Contamination with smaller nucleic acid fragments that have a length of less than 16 bp and with larger nucleic acid fragments having a length greater than 30 bp cannot be avoided. The iNAs that are too short having a length of less than 16 bp results in iNAs that do not efficiently downregulate the target RNA. An iNA that has a length that is greater than 30 bp cannot be transfected into mammalian cells because their introduction into the mammalian cells activates an interferon and protein kinase R (NCR) pathways in the cells, resulting in nonspecific gene silencing and apoptosis. Such an siRNA library may contain a high frequency of undesirable ("junk") clones which may not only drastically impair the overall efficiency of the approach, but also seriously compromise the integrity of the data that are generated. Thus, this approach is not ideal for screening for the best siRNA sequence site for functional genomics and RNAi therapeutics.

An ideal iNA library, especially a gene-specific library, should contain every site represented by multiple overlapping sequences, and individual sequences should have the widely accepted rational length of 19-23 bp, and should easily and simply be amplified by PCR to meet a high-throughput library construction format, accelerating the screenings for the best siRNA sequence site for functional genomics and RNAi therapeutics. Thus, there is a need to provide for a method for to produce a library or pool iNA constructs having a length of 19-23 bps, which can be produced in a high-throughput manner, which covers the target sequence of an RNA.

SUMMARY

An object of the present invention is to provide a type III restriction/modification enzyme mediated PCR high-throughput method for preparing an iNA pool from a DNA sample (cDNA or genomic DNA and so on) for RNAi therapeutic targets screening. The resulting siRNA polynucleotide pool has iNAs constructing ranging in length from 16 to 27 bp, more preferably, from 21~23 bp. The pool of iNA constructs completely mimics the length of siRNA naturally generated by Dicer enzyme in living cells. This overcomes the under-representation of all possible iNA constructs produced by conventional siRNA polynucleotide pool construction approaches, which are mediated by a type II restriction enzyme-MmeI, in which the longest siRNA generated is 18-20 bp in length.

The type III restriction enzyme-EcoP15I can cleave maximal nucleic acid fragment having a length of 25-27 bp of DNA outside of their recognition site. Currently no one uses any type III restriction/modification enzymes for siRNA library construction mainly due to two technical difficulties: a.) the cleavage product having 25-27 bp is the ideal length for an iNA of 19-23 bp which is a widely accepted rational length of an siRNA; b.) two inversely oriented recognition sites of type III restriction/modification enzymes is required for effective cleavage (using EcoP15I as an example):

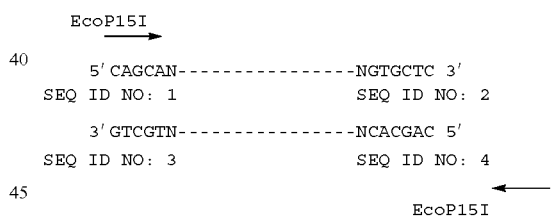

Another object of the present invention is to provide an artificial oligonucleotide shaped in a loop after self-annealing (Loop-1 linkers) containing the recognition sites of a type III restriction/modification enzyme and a type II restriction enzyme. The general structure formula of Loop-1 linker(s) is:

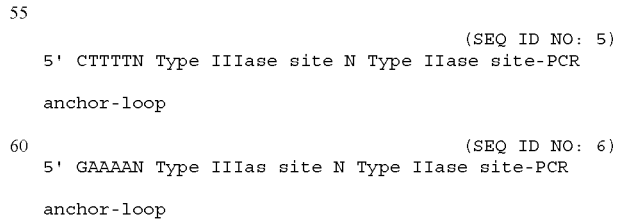

Where: in SEQ ID NO: 5, there can be 0 to 20 nucleotides between the 'C' and the first 'T' at the 5' end at the 3' end there can be an additional nucleotides ranging from 0 to 20 after the 3' N;

In SEQ ID NO: 6, there can be 0 to 20 nucleotides between the 'G' and the first 'T' at the 3' end, and 0 to 20 nucleotides after the A at the 5' end;

N is any nucleotide bases preferably G, C, T, or A;

Type IIase: type III restriction/modification enzyme;

Type IIase: type II restriction enzyme.

Another object of the present invention is to provide another artificial oligonucleotide shaped in a loop after self-annealing (Loop-2 linker) containing a type II restriction enzyme recognition sequences.

The general structure formula of Loop-2 linker is:

(SEQ ID NO: 5) 5'CTTTTN Type IIase site-PCR anchor-loop having 0-20 nucleotides between 'C' and first 'T' and 0-20 nucleotides after the 5' 'T'

(SEQ ID NO: 6) 3' GAAAAN Type IIase site-PCR anchor-loop having 0-20 nucleotides between 'G' and the first 'A' and 0-20 nucleotides after the final 3' 'A'.

Where N is a nucleotide base preferably G, C, T, or A; and Type IIase is a type II restriction enzyme.

Another object of the present invention is to provide a protocol for a PCR based high-throughput method for preparing an siRNA polynucleotide pool from a DNA sample, comprised of:

a.) Partially digesting cDNA or genomic DNA with DNaseI in the presence of $Mn^{2+}$ producing DNA constructs that are blunt-ended;

b.) Ligating Loop-1 linker(s) to one end of the blunted-ended DNA constructs;

c.) Amplifying by PCR the DNA constructs with a single primer that is a portion of homologous sequences to the antisense strand of the Loop-1 linker(s) (the strand with a polyA stretch) producing DNA constructs containing double type III restriction/modification enzyme sites (e.g., EcoP15I) in inversed orientation at the DNA both ends, which are cleavable; and d.) Cleaving the DNA constructs with a type III restriction/modification enzyme (e.g., EcoP15I). The enzyme cleaves a maximal 25-27 bp of DNA outside of their recognition sites. The resulting siRNA polynucleotide pool distributed from 19 to 23 bp in length by adjusting the adjacent number of poly (A/T) sequences in the Loop-1 linker(s);

e.) Blunt-ending by filling in with a DNA polymerase in the present of dNTPs;

f.) Loop-2 linker ligation. A type II restriction site (e.g., Fok1) is included in the Loop-2;

g.) Second PCR amplification with 5' Loop-1 and 3' Loop-2 primers;

h.) A type II restriction enzyme (e.g., FokI in both loops) digestion to generate over polyA ($A_4$) sticky ends (cohesive ends) at both 5' ends;

i.) Inserting the type II restriction enzyme digested constructs to a pre-prepared siRNA expression vector with polyT (especially $T_4$) sticky or cohesive ends at both 3' ends, flanked by two tandem RNA polymerase III promoters such as U6 and H1, to complete an siRNA polynucleotide pool construction. Poly $(A/T)_5$ act as the initial and termination signals for RNA polymerase III promoters after cloning.

DEFINITIONS AND DESCRIPTION

Figure 1:
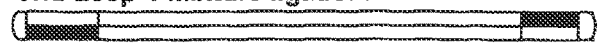
FIG. 1 A Schematic Diagram of Technical Flow-Chart and the Structure of Loop-1 Linker(s) (using EcoP15I as an example)
Figure 1:
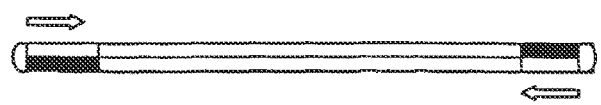
Figure 1:
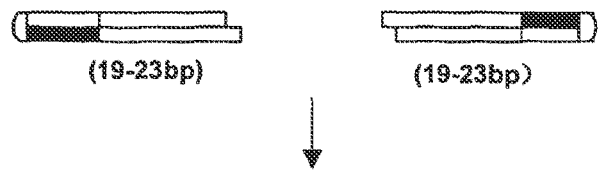
Figure 1:
Figure 1:
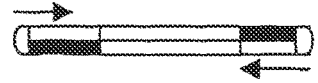
Figure 1:
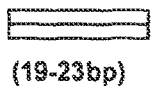
Figure 1:
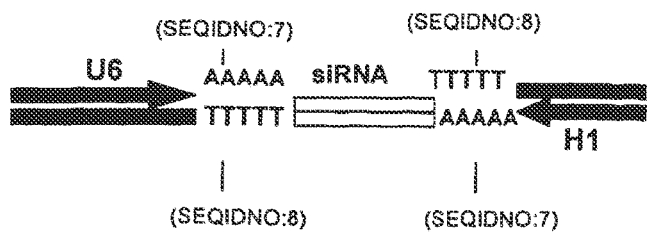

Definitions of technical terms provided herein should be construed to include without recitation those meanings associated with these terms known to those skilled in the art, and are not intended to limit the scope of the invention.

The use herein of the terms "a," "an," "the," and similar terms in describing the invention, and in the claims, are to be construed to include both the singular and the plural. The terms "comprising," "having," "including," and "containing" are to be construed as open-ended terms which mean, for example, "including, but not limited to."

Recitation of a range of values herein refers individually to each and any separate value falling within the range as if it were individually recited herein, whether or not some of the values within the range are expressly recited. Specific values employed herein will be understood as exemplary and not to limit the scope of the invention.

As used herein, the term interfering nucleic acid (iNA) refers to a nucleic acid duplexes having a sense and antisense strand, which when entered into a RISC complex induces enzymatic degradation of mRNA. Generally each strand contains predominantly RNA nucleotides but the strands can contain RNA analogs, RNA and RNA analogs, RNA and DNA, RNA analogs and DNA, or one strand that is completely DNA and one strand that is RNA as long as the iNA construct induces enzymatic degradation of a homologous mRNA.

The term "short interfering nucleic acid", "iNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Zamore et al., 2000, Cell, 101, 25-33; Bass, 2001, Nature, 411, 428-429; Elbashir et al, 2001, Nature, 411, 494-498; and Kreutzer et al., International PCT Publication No. WO 00/44895; Zernicka-Goetz et al., International PCT Publication No. WO 01/36646; Fire, International PC7 Publication No. WO 99/32619; Plaetinck et al., International PCT Publication No. WO 00/01846; Mello and Fire, International PCF Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002. RNA, 8, 842-850; Reinhart et al., 2002, Gene & Dev., 16, 1616-1626; and Reinhart & Bartel, 2002, Science, 297, 1831), For example the iNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof.

The iNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the iNA molecule are complementary to the target nucleic acid or a portion thereof). Alternatively, the iNA is assembled from a single oligonucleotide, where thoself-complementary sense and antisense regions of the iNA are linked by means of a nucleic acid based or non-nucleic acid-based linker(s).

The iNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The iNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active iNA molecule capable of mediating RNAi. The iNA can also comprise a single stranded polynucleotide having nucleotide sequence complementary to nucleotide sequence in a target nucleic acid molecule or a portion thereof (for example, where such iNA molecule does not require the presence within the iNA molecule of nucleotide sequence corresponding to the target nucleic acid sequence or a portion thereof), wherein the single stranded polynucleotide can further comprise a terminal phosphate group, such as a 5'-phosphate (see the example Martinez et al., 2002, Cell., 110, 563-574 and Schwarz et al., 2002, Molecular Cell, 10, 537-568), or 5',3'-diphosphate. In certain embodiments, the iNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der wools interactions, hydrophobic interactions, and/or stacking interactions. In certain embodiments, the iNA molecules of the invention comprise nucleotide sequence that is complementary to nucleotide sequence of a target gene. In another embodiment, the iNA molecule of the invention interacts with nucleotide sequence of a target gene in a manner that causes inhibition of expression of the target gene.

As used herein, iNA molecules need not be limited to those molecules containing only RNA, but further encompasses chemically modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such iNA molecules that do not require the presence of ribonucleotides within the iNA molecule to support RNAi can however have an attached linker or linkers or other attached or associated groups, moieties, or chains containing one or more nucleotides with 2'-OH groups. Optionally, iNA molecules can comprise ribonucleotides at about 5, 10, 20, 30, 40, or 50% of the nucleotide positions. The modified short interfering nucleic acid molecules of the invention can also be referred to as short interfering modified Oligonucleotides "siMON." As used herein, the term iNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post-transcriptional gene silencing, translational inhibition, or epigenetics. For example, iNA molecules of the invention can be used to epigenetically silence genes at both the post-transcriptional level or the pre-transcriptional level. In a non-limiting example, epigenetic regulation of gene expression by iNA molecules of the invention can result from iNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

As used herein, the term "iNA duplex" is a generic term used throughout the specification to include interfering nucleic acids (iNAs), hairpin iNAs which can be cleaved in vivo to form iNAs. The iNA duplexes herein also include expression vectors (also referred to as iNA expression vectors) capable of giving rise to transcripts that form iNA duplexes or hairpin iNAs in cells, and/or transcripts, which can produce iNAs in vivo. Optionally the iNA include single strands that form a duplex by a hairpin-loop or double strands of iNA. The iNA is a double-stranded polynucleotide molecule comprising self-complementary sense and anti-sense regions, wherein the antisense region comprises a nucleotide sequence that is complementary to a nucleotide sequence in a target ribonucleic acid molecule for down regulating expression, or a portion thereof. The sense strand or antisense strand have one or more nicks or nucleotide. The terminal structure of iNA may be either blunt or cohesive (overhanging) as long as the iNA can silence the target mRNA. The cohesive (overhanging) end structure is not limited only to the 3' overhang, as the 5'overhanging structure may be included as long as it is capable of inducing the RNAi effect. In addition, the number of overhanging nucleotides is not limited to the reported 2 or 3, but can be any number as long as the overhang is capable of inducing the RNAi effect. For example, the overhang may be 1 to 8, or 2 to 4 nucleotides.

As used herein the length of the iNA duplex is determined by counting the number of nucleotides in the duplex starting at the first base-pair at the 5' end of the sense strand and ending at the last base-pair at the 3' end of the sense strand.

In genetics, microRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Modified nucleotides in an iNA molecule can be in the antisense strand, the sense strand, or both. For example, modified nucleotides can have a Northern conformation (e.g., Northern pseudorotaiion cycle, see, for example, Saenger, Principles of Nucleic Acid Structure, Springer-Verlag ed., 1984). Examples of nucleotides having a Northern configuration include locked nucleic acid (LNA) nucleotides (e.g., 2'-O, 4'-C-methylene-(D-ribofuranosyl) nucleotides), 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, and 2'-O-methyl nucleotides. Chemically modified nucleotides can be resistant to nuclease degradation while at the same time maintaining the capacity to mediate RNAi. A conjugate molecule attached to a chemically-modified iNA molecule is a polyethylene glycol, human serum albumin, or a ligand for a cellular receptor that can mediate cellular uptake. Examples of specific conjugate molecules contemplated by the instant invention that can be attached to chemically-modified iNA molecules are described in Vargeese, et al., U.S. Patent Publication No. 20030130186 and U.S. Patent Publication No. 20040110296, which are each hereby incorporated by reference in their entirety.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2-O-methyl, 2'-H, nucleotide base modifications. For a review see Usman and Cedergren, TIBS 17:34, 1992; Usman, et al, Nucleic Acids Symp. Ser. 31:163, 1994; Burgin, et al, Biochemistry 35:14090, 1996. Sugar modification of nucleic acid molecules have been extensively described in the art. See Eckstein et al., International Publication PCT No. WO 92/07065; Perrault, et al. Nature 344:565-568, 1990; Pieken, et al. Science 253:314-317, 1991; Usman and Cedergren, Trends in Biochem. Sci. 17:334-339, 1992; Usman et al. International Publication PCT No. WO 93/15187; Sproat, U.S. Pat. No. 5,334,711 and Beigelman, et al., J. Biol. Chem. 270:25702., 1995; Beigelman, et al., International PCT Publication No. WO 97/26270; Beigelman, et al., U.S. Pat. No. 5,716,824; Usman, et al., U.S. Pat. No. 5,627,053; Woolf, et al., International PCT Publication No. WO 98/13526; Thompson, et al., Karpeisky, et al, Tetrahedron Lett. 39:1131, 1998; Earnshaw and Gait, Biopolymers (Nucleic Acid Sciences) 48:39-55, 1998; Verma and Eckstein, Annu. Rev. Biochem. 67:99-134, 1998; and Burlina, et al., Bioorg. Med. Chem. 5:1999-2010, 1997. Such publications describe general methods and strategies to determine the location of incorporation of sugar, base and/or phosphate modifications and the like into nucleic acid molecules without modulating catalysis. In view of such teachings, similar modifications can be used as described herein to modify the iNA nucleic acid molecules of the claimed duplexes so long as the ability of iNA to promote RNAi in cells is not significantly inhibited.

The iNA duplexes may contain modified iNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyi, substitutions. For a review of oligonucleotide backbone modifications, see Hunziker and Leumann, Nucleic Acid Analogues: Synthesis and Properties, in Modern Synthetic Methods, VCH, 1995, pp. 331-417, and Mesmaeker, et al., "Novel Backbone Replacements for Oligonucleotides, in Carbohydrate Modifications in Antisense Research," ACS, 1994, pp. 24-39. Examples of chemical modifications that can be made in an iNA include phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. The antisense region of a iNA molecule can include a phosphorothioate internucleotide linkage at the 3'-end of said antisense region. The antisense region can comprise about one to about five phosphorothioate internucleotide linkages at the 5'-end of said antisense region. The 3'-terminal nucleotide overhangs of a iNA molecule can include ribonucleotides or deoxyribonucleotides that are chemically-modified at a nucleic acid sugar, base, or backbone. The 3'-terminal nucleotide overhangs can include one or more universal base ribonucleotides. The 3'-terminal nucleotide overhangs can comprise one or more acyclic nucleotides. For example, a chemically-modified iNA can have 1, 2, 3, 4, 5, 6, 7, 8, or more phosphorothioate internucleotide linkages in one strand, or can have 1 to 8 or more phosphorothioate internucleotide linkages in each strand. The phosphorothioate internucleotide linkages can be present in one or both oligonucleotide strands of the NA duplex, for example in the sense strand, the antisense strand, or both strands. in some embodiments, a iNA molecule includes 1, 2, 3, 4, 5, 6, 7, 8, 9, 10, or more purine phosphorothioate internucleotide linkages in the sense strand, the antisense strand, or in both strands.

The iNA molecules, which can be chemically-modified, can be synthesized by: (a) synthesis of two complementary strands of the iNA molecule; and (b) annealing the two complementary strands together under conditions suitable to obtain a double-stranded iNA molecule. In some embodiments, synthesis of the complementary portions of the iNA molecule is by solid phase oligonucleotide synthesis, or by solid phase tandem oligonucleotide synthesis.

The term "nucleotide" as used herein, refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group, The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman &. Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, .beta.-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra).

By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule. Nucleotides are organic compounds comprised of three joined structures: a nitrogenous base, a sugar, and a phosphate group. The most common nucleotides can be divided into two groups (purines and pyrimidines) based on the structure of the nitrogenous base. The joined sugar is either ribose or deoxyribose. A nucleotide is composed of a ring of nitrogen, carbon and oxygen atoms, a five-carbon sugar (together referred to as a nucleoside) and one phosphate group. The name of the nucleotide is determined by its base. For example an adenine (A) nucleotide has an adenine base, a guanine (G) nucleotide has a guanine base, a thymine (T) nucleotide has a thymine base, a uracil (U) nucleotide has a uracil base, and a cytosine (C) nucleotide has a cytosine base.

A strand of DNA contains nucleotides and a DNA molecule is made up of 2 polynucleotide chains arranged on the double helix (the backbone). These nucleotides are composed of three parts: a phosphate, a sugar (deoxyribose), and a type of compound base. The deoxyribose and phosphate form the backbone of nucleic acid (the side of the ladder) while the base connect the two polynucleotide chains (like the rungs of the ladder). There are four main types of bases, adenine, guanine, thymine and cytosine but they are just referred to by the first letter in their name, A, G, T and C respectively.

Ribonucleic acid (RNA) is a nucleic acid that is comprised of a long chain of nucleotide units. Each nucleotide consists of a nitrogenous base, a ribose sugar, and a phosphate. RNA is very similar to DNA, but differs in a few important structural details: in the cell, RNA is usually single-stranded, while DNA is usually double-stranded; RNA nucleotides contain ribose while DNA contains dexoyribose (a type of ribose that lacks one oxygen atom); and RNA has the base uracil rather than thymine that is present in DNA. RNA is transcribed from DNA by enzymes called RNA polymerases and is generally further processed by other enzymes.

Oligonucleotides (e.g., certain modified oligonucleotides or portions of oligonucleotides lacking ribonucleotides) are synthesized using protocols known in the art, for example as described in Caruthers, et al, Methods in Enzymology 211:3-19, 1992; Thompson, et al., International PCT Publication No. WO 99/54459; Wincott, et al., Nucleic Acids Res. 23:2677-2684, 1995; Wincott, et al., Methods Mol. Bio. 74:59, 1997; Brennan, et al., Biotechnol Bioeng. 61:33-45, 1998; and Brennan, U.S. Pat. No. 6,001,311. Synthesis of RNA, including certain iNA molecules of the invention, follows general procedures as described, for example, in Usman, et al., J. Am. Chem. Soc. 109:7845, 1987; Scaringe, et al., Nucleic Acids Res. 18:5433, 1990; and Wincott, et al, Nucleic Acids Res. 23:2677-2684, 1995; Wincott, et al, Methods Mol. Bio. 74:59, 1997. The double-stranded structure may be formed by self-complementary iNA strand such as occurs for a hairpin RNA or by annealing of two distinct complementary iNA strands.

"Overlapping" refers to when two iNA fragments have sequences which overlap by a plurality of nucleotides on one strand, for example, where the plurality of nucleotides (nt) numbers as few as 2-5 nucleotides or by 5-10 nucleotides or more.

"One or more iNAs" refers to iNAs that differ from each other on the basis of primary sequence.

By "target site" or "target sequence" or "targeted sequence" is meant a sequence within a target nucleic acid (e.g., RNA) that is "targeted" for cleavage mediated by an iNA duplex which contains sequences within its antisense region that are complementary to the target sequence.

A hybrid iNA molecule is an iNA that is a double-stranded nucleic acid. Instead of a doable-stranded RNA molecule, a hybrid iNA is comprised of an RNA strand and a DNA strand, Preferably, the RNA strand is the antisense strand as that is the strand that binds to the target mRNA. The hybrid iNA created by the hybridization of the DNA and RNA strands have a hybridized complementary portion and preferably at least one 3' overhanging end.

To "modulate gene expression" as used herein is to up-regulate or down-regulate expression of a target gene, which can include upregulation or down-regulation of mRNA levels present in a cell, or of mRNA translation, or of synthesis of protein or protein subunits, encoded by the target gene.

The terms "inhibit," "down-regulate," or "reduce expression," as used herein mean that the expression of the gene, or level of RNA molecules or equivalent RNA molecules encoding one or more proteins or protein subunits, or level or activity of one or more proteins or protein subunits encoded by a target gene, is reduced below that observed in the absence of the nucleic acid molecules (e.g., iNA) of the invention, "Gene silencing" as used herein refers to partial or complete inhibition of gene expression in a cell and may also be referred to as "gene knockdown." The extent of gene silencing may be determined by methods known in the art, some of which are summarized in International Publication No. WO 99/32619.

"Restriction Enzyme" A restriction enzyme (or restriction endonuclease) is an enzyme that cuts double-stranded DNA at specific recognition nucleotide sequences known as restriction sites. Such enzymes, found in bacteria and archaca, are thought to have evolved to provide a def mechanism against invading viruses. To cut the DNA, a restriction enzyme makes two incisions, once through each sugar-phosphate backbone (i.e. each strand) of the DNA double helix. Restriction endonucleases are categorized into three general groups (Types I, II and III) based on their composition and enzyme cofactor requirements, the nature of their target sequence, and the position of their DNA cleavage site relative to the target sequence.

The term "complementarity" refers to the ability of a nucleic acid to form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., RNA interference, enzymatic nucleic acid cleavage, antisense or triple helix inhibition. Determination of binding free energies for nucleic acid molecules is well known in the art (see, e.g., Turner et at., 1987, CSH Symp. Quant. Biol. LII pp. 123-133; Frier et al., 1986, Proc. Nat, Acad. Sci. USA 83:9373-9377; Turner et al., 1987, J. Am. Chem. Soc. 109:3783-3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

By "RNA" is meant a molecule comprising at least one ribonucleotide residue. By "ribonucleotide" is meant a nucleotide with a hydroxyl group at the 2' position of a .beta.-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "ribonucleotide" or "2'-OH" is meant a nucleotide with a hydroxyl group at the 2' position of a β-D-ribo-furanose moiety.

Joining linear DNA fragments together with covalent bonds is called ligation or ligating the fragments together. More specifically, DNA ligation involves creating a phosphodiester bond between the 3' hydroxyl of one nucleotide and the 5' phosphate of another, The enzyme used to ligate DNA fragments is T4 DNA ligase, which originates from the T4 bacteriophage. This enzyme will ligate DNA fragments having overhanging, cohesive ends that are annealed together, as in the EcoRI example below—this is equivalent to repairing "nicks" in duplex DNA. T4 DNA ligase will also ligate fragments with blunt ends, although higher concentrations of the enzyme are usually recommended for this purpose.

A restriction digest is a procedure used in molecular biology to prepare DNA for analysis or other processing. It is also known as DNA fragmentation. It uses a number of restriction enzymes to selectively cleave strands of DNA into shorter fragments, or to isolate short fragments of interest. The resulting digested DNA is very often selectively amplified using PCR, making it more suitable for analytical techniques such as agarose gel electrophoresis, and chromatography. It is used in genetic fingerprinting, and RFLP analysis.

A given restriction enzyme cuts DNA segments within a specific nucleotide sequence. These recognition sequences are typically four, six, eight, ten, or twelve nucleotides long. Because there are only so many ways to arrange the four nucleotides which compose DNA (Adenine, Thymine, Guanine and Cytosine) into a four- to twelve-nucleotide sequence, recognition sequences tend to occur by chance in any long sequence. Restriction enzymes specific to hundreds of distinct sequences have been identified and synthesized for sale to laboratories, and as a result, several potential "restriction sites" appear in almost any gene or locus of interest on any chromosome. Furthermore, almost all artificial plasmids include an (often entirely synthetic) polylinder (also called "multiple cloning site") that contains dozens of restriction enzyme recognition sequences within a very short segment of DNA. This allows the insertion of almost any specific fragment of DNA into plasmid vectors, which can be efficiently "cloned" by insertion into replicating bacterial cells.

After restriction digest, DNA can then be analysed using gel electrophoresis. In gel electrophoresis, a sample of DNA is first "loaded" onto a slab of agarose gel (literally pipetted into small wells at one end of the slab). The gel is then subjected to an electric field, which draws the negatively charged DNA across it. The molecules travel at different rates and therefore stop at different distances) depending on their net charge (more highly charged particles travel further), and size (smaller particles travel further). Since none of the four nucleotide bases carry any charge, net charge becomes insignificant and size is the main factor affecting rate of diffusion through the gel. Net charge in DNA is produced by the sugar-phosphate backbone.

Polymerase chain reaction (PCR) is a technique widely used in molecular biology, it derives its name from one of its key components, a DNA polymerase used to amplify a piece of DNA by in vitro enzymatic replication. As PCR progresses, the DNA thus generated is itself used as a template for replication. This sets in motion a chain reaction in which the DNA template is exponentially amplified. With PCR it is possible to amplify a single or few copies of a piece of DNA across several orders of magnitude, generating millions or more copies of the DNA piece. PCR can be extensively modified to perform a wide array of genetic manipulations.

PCR is very versatile. Many types of samples can be analyzed for nucleic acids. Most PCR uses DNA as a target, rather than RNA, because of the stability of the DNA molecule and the ease with which DNA can be isolated. Almost all PCR applications employ a heat-stable DNA polyrnerase, such as Taq polymerase, an enzyme originally isolated from the bacterium *Thermus aquaticus*. This DNA polymerase enzymatically assembles a new DNA strand from DNA building blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps.

These thermal cycling steps are necessary to physically separate the strands (at high temperatures) in a DNA double helix (DNA melting) used as template during DNA synthesis (at lower temperatures) by the DNA polymerase to selectively amplify the target DNA. The selectivity of PCR results from the use of primers that are complementary to the DNA region targeted for amplification under specific thermal cycling conditions. PCR is used to amplify specific regions of a DNA strand (the DNA target). This can be a single gene, a part of a gene, or a non-coding sequence. Most PCR methods typically amplify DNA fragments of up to 10 kilo base pairs (kb), although some techniques allow for amplification of fragments up to 40 kb in size.

A basic PCR set up requires several components and reagents. These components include:

DNA template that contains the DNA region (target) to be amplified.

Two primers, which are complementary to the DNA regions at the 5' (five prime) or 3' (three prime) ends of the DNA region.

Taq polymerase or another DNA polymerase with a temperature optimum at around 70° C.

Deoxynucleoside triphosphates (dNTPs), the building blocks from which the DNA polymerases synthesizes a new DNA strand.

Buffer solution providing a suitable chemical environment for optimum activity and stability of the DNA polymerase.

Divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis.

Monovalent cation potassium ions.

PCR is commonly carried out in a reaction volume of 10-200 μL in small reaction tubes (0.2-0.5 mL volumes) in a thermal cycler. The thermal cycler heats and cools the reaction tubes to achieve the temperatures required at each step of the reaction (see below). Many modem thermal cyders make use of the Peletier effect which permits both heating and cooling of the block holding the PCR tubes simply by reversing the electric current. Thin-walled reaction tubes permit favorable thermal conductivity to allow for rapid thermal equilibration. Most thermal cyclers have heated lids to prevent condensation at the top of the reaction tube. Older thermocyclers lacking a heated lid require a layer of oil on top of the reaction mixture or a ball of wax inside the tube. The PCR usually consists of a series of 20 to 40 repeated temperature changes called cycles; each cycle typically consists of 2-3 discrete temperature steps. Most commonly PCR is carried out with cycles that have three temperature steps. The cycling is often preceded by a single temperature step (called hold) at a high temperature (>90° C.), and followed by one hold at the end for final product extension or brief storage. The temperatures used and the length of time they are applied in each cycle depend on a variety of parameters. These include the enzyme used for DNA synthesis, the concentration of divalent ions and dNTPs in the reaction, and the melting temperature (Tm) of the primers.

Initialization step: This step consists of heating the reaction to a temperature of 94-96° C. (or 98° C. if extremely thermostable polymerases are used), which is held for 1-9 minutes. It is only required for DNA polymerases that require heat activation by hot-start PCR.

Denaturation step: This step is the first regular cycling event and consists of heating the reaction to 94-98° C. for 20-30 seconds. It causes melting of DNA template and primers by disrupting the hydrogen bonds between complementary bases of the DNA strands, yielding single strands of DNA.

Annealing step: The reaction temperature is lowered to 50-65° C. for 20-40 seconds allowing annealing of the primers to the single-stranded DNA template. Typically the annealing temperature is about 3-5 degrees Celsius below the Tm of the primers used. Stable DNA-DNA hydrogen bonds are only formed when the primer sequence very closely matches the template sequence. The polymerase binds to the primer-template hybrid and begins DNA synthesis.

Extension/elongation step: The temperature at this step depends on the DNA polyrnerase used; Taq polymerase has its optimum activity temperature at 75-80° C., and commonly a temperature of 72° C. is used with this enzyme. At this step the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time depends both on the DNA polymerase used and on the length of the DNA fragment to be amplified. As a rule-of-thumb, at its optimum temperature, the DNA polymerase will polymerize a thousand bases per minute. Under optimum conditions, i.e., if there are no limitations due to limiting substrates or reagents, at each extension step, the amount of DNA target is doubled, leading to exponential (geometric) amplification of the specific DNA fragment.

Final elongation: This single step is occasionally performed at a temperature of 70-74° C. for 5-15 minutes after the last PCR cycle to ensure that any remaining single-stranded DNA is fully extended.

Final hold: This step at 4-15° C. for an indefinite time may be employed for short-term storage of the reaction.

To check whether the PCR generated the anticipated DNA fragment (also sometimes referred to as the amplimer or amplicon), agarose gel electrophoresis is employed for size separation of the PCR products. The size(s) of PCR products is determined by comparison with a DNA ladder (a molecular weight marker), which contains DNA fragments of known size, run on the gel alongside the PCR products. See Joseph Sambrook and David W. Russel (2001). Molecular Cloning: A Laboratory Manual, 3rd ed., Cold Spring Harbor, N.Y.: Cold Spring Harbor Laboratory Press. Chapter 8: In vitro Amplification of DNA by the Polymerase Chain Reaction Type I Type I restriction enzymes were the first to be identified and are characteristic of two different strains (K-12 and B) of *E. coli*. These enzymes cut at a site that differs, and is some distance (at least 1000 bp) away, from their recognition site. The recognition site is asymmetrical and is composed of two portions—one containing 3-4 nucleotides, and another containing 4-5 nucleotides—separated by a spacer of about 6-8 nucleotides.

Type II

Typical type II restriction enzymes differ from type I restriction enzymes in several ways. They are composed of only one subunit, their recognition sites are usually undivided and palindromic and 4-8 nucleotides in length, they recognize and cleave DNA at the same site, and require only $Mg^{2+}$ as a cofactor. There are subcategories based on deviations front typical characteristics of type II enzymes. These subgroups are defined using a letter suffix.

Type IIB restriction enzymes (e.g. BcgI and BpII) are multimers containing more than one subunit. They cleave DNA on both sides of their recognition to cut out the recognition site. They require both AdoMet and Mg.sup.2+ cofactors. Type IIE restriction endonucleases (e.g. NaeI) cleave DNA following interaction with two copies of their recognition sequence. One recognition site acts as the target for cleavage, while the other acts as an allosteric effector that speeds up or improves the efficiency of enzyme cleavage. Similar to type IIE enzymes, type IIF restriction endonucleases (e.g. NgoMIV) interact with two copies of their recognition sequence but cleave both sequences at the same time. Type IIG restriction endonucleases (Eco57I) do have a single subunit, like classical Type II restriction enzymes, but require the cofactor AdoMet to be active. Type IIM restriction endonucleases, such as DpnI, are able to recognize and cut methylated DNA. Type IIS restriction endonucleases (e.g. FokI) cleave DNA at a defined distance from their non-palindromic asymmetric recognition sites.

These enzymes may function as dimers. Similarly, Type IIT restriction enzymes (e.g., Bpu10I and Bs1I) are composed of two different subunits. Sonic recognize palindromic sequences while others have asymmetric recognition sites.

Type III

Type III restriction enzymes (e.g. EcoP15 and EcoP15I) recognize two separate non-palindromic sequences that are inversely oriented. They cut DNA about 20-30 base pairs after the recognition site. These enzymes contain more than one subunit and require AdoMet and ATP cofactors for their roles in DNA methylation and restriction, respectively.

"Recognition site" Restriction enzymes recognize a specific sequence of nucleotides and produce a double-stranded cut in the DNA. While recognition sequences vary widely, with lengths between 4 and 8 nucleotides, many of them are palindromic; that is, the sequence on one strand reads the same in the reverse direction on the complementary strand. The meaning of "palindromic" in this context is different from what one might expect from its linguistic usage: GTAATG (SEQ ID NO:68) is not a palindromic DNA sequence, but GTATAC (SEQ ID NO:69) is [GTATAC (SEQ ID NO:69 is complementary to CATATG (SEQ ID NO:70)].

Recognition sequences in DNA differ for each restriction enzyme, producing differences in the length, sequence and strand orientation (5' end or the 3' end) of a sticky-end "overhang" of an enzyme restriction.

A vector is any vehicle used to transfer foreign genetic material into another cell. The vector itself is generally a DNA sequence that consists of an insert (transgene) and a larger sequence that serves as the "backbone" of the vector. The purpose of a vector to transfer genetic information to another cell is typically to isolate, multiply, or express the insert in the target cell. Vectors called expression vectors (expression constructs) specifically are for the expression of the transgene in the target cell, and generally have a promotersequence that drives expression of the transgene. The expression may be of a polypeptide, protein or RNA.

An iNA expression vector is a vector that expresses an iNA.

A DNA construct is a DNA that is to be expressed when inserted into a vector and transfected into a cell.

Insertion of a vector into the target cell is generally called transfection, although insertion of a viral vector is often called transduction.

In the Loop-1 linker(s) of present invention as described in FIG. 1 and "The general structure formula" described above, the poly(T/A) sequences between EcoP15I and DNA inserts play three key roles:

a.) The resulting DNA insert length after EcoP15I cleavage can be modified to have a length of from 19-23 bp by the addition or deletion of poly(T/A) sequences between EcoP15I in Loop-1 and DNA substrates. If one uses a Loop-1 linker only with a distinct poly(T/A) number, the length of DNA insert can also be fixed at a certain length to construct an siRNA polynucleotide pool at a distinct length, or mix all Loop-1 linkers together to generate an siRNA polynucleotide pool having a 19-23 bp size distribution, according to the needs. Using this method an siRNA polynucleotide pool can be produced in which the lengths of the iNA constructs can be varied by the addition or deletion of the A/T sequences in Loop-1 linker(s) resulting in iNA pools being constructed in which the lengths of the constructs are 16-18 bp or 24-27 bp;

b.) Generating polyA ($A_4$) cohesive ends at both 5' ends by FokI, a type II restriction enzyme, conducting a poly T/A cloning. For the construction of a 24-27 bp iNA polynucleotide pool construction, other type restriction enzymes can be employed to create the corresponding cloning sites;

c.) Generating the initiation and termination signals of RNA polymerase III promoters. After the iNA polynucleotide inserts are cloned into a siRNA expression vector, the "AAAAA" (SEQ ID NO: 7) (an initiation signal) and "TTTTT" (SEQ ID NO: 8)(a termination signal) of the promoters are generated. There are no additional cloning sequences between RNA polymerase III (U6 and H1) promoters and DNA inserts, which can increase specificity of RNAi therapeutic targets screening.

The number of "N" between EcoP15I and FokI maintains the A.sub.4 adhesive ends (over $A_4$ hanging ends at both 5' ends). As soon as ligation into an siRNA expression vector which has T5/A1 cohesive ends, the length of initiation signal [AAAAA (SEQ ID NO:7)] and termination signal [TTTTT (SEQ ID NO: 8)] for RNA polymerase III promoters (U6 and H1) are created.

Adding an additional "G" before the initiation signal "AAAAA" (SEQ ID NO: 7) of RNA polymerase III promoters improves an siRNA transcription efficiency. A feature of the present invention is that Loop-1 linkers contain a "G" before Poly(A), except for construction of 23 bp siRNA polynucleotide pool. It is widely accepted that placing "G" before the initial signal "AAAAA" (SEQ ID NO: 7) enhances RNA polymerase III promoter activity, especially for the U6 promoter. However, the "G" needs to be omitted to maintain siRNA polynucleotide 23 bp in length by Loop-1 linker and can be added to an siRNA expression vector. If needed, for 24-27 bp siRNA polynucleotide pool construction, one should place the initiation/termination signals together with its enhancing base "G" into an siRNA expression vector. In this case an appropriate cloning site has to be selected in both Loop-1 linker(s) and vector to conduct an efficient cloning. The present invention provides unlimited formats, especially with the future appearance of other type III restriction enzymes that have longer cleavage outside of their recognition sequences than EcoP15I or EcoP15.

The PCR anchor and the loop structure designed in Loop-1 linker(s) are used to select a correct orientation for type III restriction/modification enzyme cleavage. As mentioned above, the type III restriction/modification enzymes require two 5' sequences in inversed orientations within the same DNA molecule to accomplish cleavage. Single primer PCR enables to select such molecules. For a successful single primer-based PCR selection, a loop shaped structure is helpful. Unlike a tandem linker, a looped linker has no primer activity, thus ensures the single primer PCR successful.

In a preferred embodiment of the present invention there are the following steps:

1) DNA is randomly and partially digested producing blunt-ended fragments by DNase I in the presence of $Mn^{2+}$ DNase I, (RNase-free) is an endonuclease that nonspecifically cleaves DNA to produce products having 5'-phosphorylated and 3'-hydroxylated end. The concentration of DNase I for the partial digestion is 0.01~0.3 U of DNaseI per 1 g DNA depending on the length and purity of DNA as well as the source of the enzyme. Due to a nonspecific fragmentation, the resulting products are random fragments that can be a representative distribution of the siRNA polynucleotide pool generated. In the presence of $Mn^{2+}$ (a final concentration is 1 mM in a buffer, e.g., NEB buffer-2), the partially digested DNA are blunt-ended. The preferable length for downstream Loop-1 linker(s) ligation and siRNA polynucleotide pool construction is 100-300 bp.

2) Loop-1 Linker(s) ligation:

The present invention has designed various kinds of corresponding Loop-1 linker(s). They can be used in a mixture to generate 19-, 20-, 21-, 22-, and 23 bp siRNA polynucleotide pool in length simultaneously, or separately use if one has specially interest in a distinct length polynucleotide of siRNA. FIG. 1 shows the general structure of a DNA construct of a Loop-1 linker having a EcoP15I/Fok1 restriction sites. Examples of such Loop-1 constructs include:

```
For 19 bp iNA Library:
EcoP15I Fok1
                             (SEQ ID NO: 79)
5' CTTTTTTTCTGCTG CATCC (SEQ ID NO: 80)
3' GAAAAAAAGACGAC GTAGG For 20 bp siRNA Library:
EcoP15I Fok1
                             (SEQ ID NO: 71)
5' CTTTTTTCTGCTGNCATCC (SEQ ID NO: 72)
3' GAAAAAAGACGACNGTAGG For 21 bp siRNA Library:
EcoP15I Fok1
                             (SEQ ID NO: 73)
5' CTTTTTCTGCTGNNCATCC (SEQ ID NO: 74)
3' GAAAAAGACGACNNGTAGG;

For 22 bp siRNA Library:
EcoP15I Fok1
                             (SEQ ID NO: 75)
5' CTTTTCTGCTGNNNCATCC (SEQ ID NO: 76)
3' GAAAAGACGACNNNGTAGG;

For 23 bp siRNA Library:
EcoP15I Fok1
                             (SEQ ID NO: 77)
5' TTTTCTGCTGNNNNCATCC (SEQ ID NO: 78)
3' AAAAGACGACNNNNGTAGG.
```

As described in the Loop-1 phosphate linker(s) structure, a blunt-end ligation with the partially digested DNA can be performed by any DNA ligases, more preferably, a T4 DNA ligase in the presence of ATP. The molar ratio of Loop-1 linker(s) and DNA is 10:1.

3) Single Primer PCR Amplification:

Efficient cleavage by type III restriction enzymes requires the presence of two inversely oriented substrate sites as described above. A head to head configuration in inverse orientation is required. Using EcoP15I as an Example:

(A)

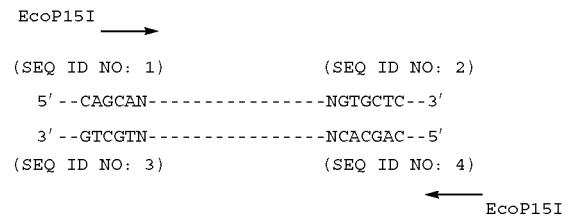

```
EcoP15I →
         (SEQ ID NO: 1)              (SEQ ID NO: 2)
         5'--CAGCAN---------------NGTGCTC--3'
         3'--GTCGTN---------------NCACGAC--5'
         (SEQ ID NO: 3)              (SEQ ID NO: 4)
                                      ← EcoP15I
```

Where there is a poly(A) sequence after the final N at the 3' end of SEQ ID NO:1, a poly(T) sequence for the first nucleotide at the 5' end of SEQ ID NO:2, a poly(T) sequence after the last nucleotide at the 5' end of SEQ ID NO:3, a poly(A) sequence before the first nucleotide at the 3' end of SEQ ID NO:4, N at the 3' end of SEQ ID NO:1 represents 25 nucleotides before the poly(A) sequence, N at the 5' end of SEQ ID NO:2 represents 27 nucleotides before the poly(T) sequence, there is a poly(T) sequence at the 5' end of SEQ ID NO:3 after the final where 'N' represents 27 nucleotides, there is a poly(A) sequence before the first 'N' at the 3' end of SEQ ID NO: 4 where 'N' represents 25 nucleotides.

However, the blunt-end ligation of Loop-1 linker(s) and DNA not only can generate the cleavable molecules (A), also generate other uncleavable molecules (B and C) as well:

```
(B):
(SEQ ID NO: 9)                                    (SEQ ID NO: 10)
5'-GTCGTCN-----------------------------------NCTGCTG-3'

3'-CAGCAGN-----------------------------------NGACGAC-5'
(SEQ ID NO: 11)                                   (SEQ ID NO: 12)
```

Where there is a poly(T) sequence after the final nucleotide at the 3' end of SEQ ID NO:9 wherein the 'N' represents 27 nucleotides, a poly(T) sequence before the first nucleotide at the 5' end of SEQ ID NO: 10 wherein 'N' represents 27 nucleotides, a poly(A) sequence after the final nucleotide at the 5' end of SEQ ID NO:11 wherein 'N' represents 25 nucleotides, a poly(A) sequence before the first nucleotide at the 3' end of SEQ ID NO:12 wherein 'N' represents 25 nucleotides.

```
(C):
(SEQ ID NO: 16)                                   (SEQ ID NO: 13)
5'-CAGCAGN-----------------------------------NGACGAC-3'

3'-GTCGTCN-----------------------------------NCTGCTC-5'
(SEQ ID NO: 14)                                   (SEQ ID NO: 15)
```

Where there is a poly(A) sequence after the final nucleotide at the 3' end of SEQ ID NO:16 wherein the 'N' represents 25 nucleotides, a poly(A) sequence before the first nucleotide at the 5' end of SEQ ID NO:13 wherein 'N' represents 25 nucleotides, a poly(T) sequence after the final nucleotide at the 5' end of SEQ ID NO:14 wherein 'N' represents 25 nucleotides, a poly(T) sequence before the first nucleotide at the 3' end of SEQ ID NO:15 wherein 'N' represents 27 nucleotides.

The present invention provides a single primer PCR amplification for selection of molecule (A) that can be cleaved. This single primer is a portion of sequences homolog to the strand with poly(A) stretch in the Loop-1 linker(s). The single primer PCR amplification completes a selection for molecule (A) that has two inversely orientated 5'-ends. The resulting PCR products are EcoP15I cleavable. The uncleveable molecules (B) and (C) are removed during the PCR process:

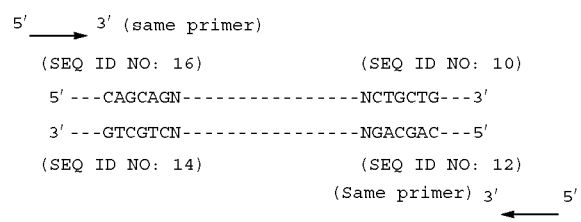

Wherein there is a poly(A) sequence after the final nucleotide at the 3' end of SEQ ID NO:16 wherein the 'N' represents 25 nucleotides, a poly(T) sequence before the first nucleotide at the 5' end of SEQ ID NO:10 wherein 'N' represents 27 nucleotides, a poly(T) sequence after the final nucleotide at the 5' end of SEQ ID NO:14 wherein 'N' represents 25 nucleotides, and a poly(A) sequence before the first nucleotide at the 3' end of SEQ ID NO:12 wherein 'N' represents 25 nucleotides.

3.) EcoP15I Digestion:

The type III restriction-modification enzyme-EcoP15I, consisting of two modification (Mod) subunits and two restriction (Res) subunits, requires the interaction of two unmethylated, inversely oriented recognition sites 5'-CAGCAG (SEQ ID NO:17) in head to head configuration to allow an efficient DNA cleavage. ATP is required for the cleavage. Cleavage efficiency is also affected by the distance between the two sites. EcoP15I can efficiently recognize the sites in distance up to 1.7 kb.

The Loop-1 linkers contain a type III restriction/modification enzyme site-EcoP15I and a type II restriction site-Fok1 adjacent to a PCR anchor. EcoP15I cleaves 25-27 bp outside of their recognition sequences, thus adjusting the number of the poly A/T sequences between EcoP15I recognition site in Loop-1 linker(s) and DNA inserts, the resulting siRNA polynucleotide pool has a distinct siRNA distribution in functional length (e.g., 19-23 bp).

4) Blunt-ending and Loop-2 linker ligation: The DNA is cohesive-ended after EcoP15I cleavage (sense strand 25 bp and antisense strand 27 bp), forming an over 5' two bases hand and can be filled-in using a DNA polymerase in the presence of dNIPs at a final concentration is 0.02 mM. After a gel purification, the ligation of blunt-ended DNA and a Loop-2 linker is catalyzed by 14 DNA ligase in the presence of ATP. The ligation products are template for the second PCR amplification.

5) Second PCR, amplification: The blunt-end ligation of EcoP15I digested siRNAs and Loop-2 linker generates the following two molecules due to different orientations:

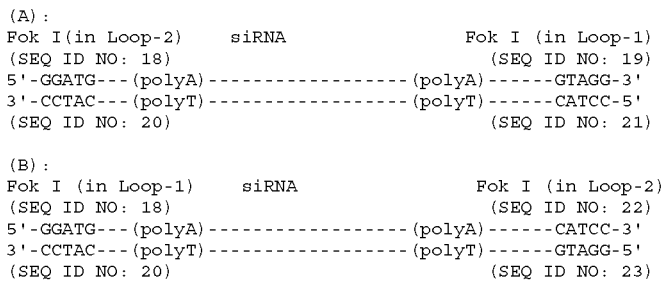

After Fok I cleavage, only molecule (B) can generate the right cloning sites as below:

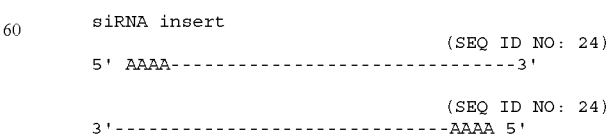

The second PCR amplification selects molecule (B) by 5' Loop-1 and 3' Loop-2 primers:

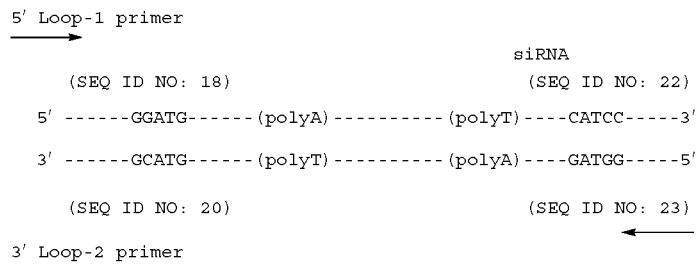

6.) FokI Digestion:

Loop-2 linker plays a role in creating a PCR anchor and a cloning site. As a type II restriction enzyme-FokI can cleave any neighboring 9-13 bp sequences, after digestion, the DNA inserts generate over $A_4$ hands at both 5' ends as described in (5.).

Figure 2:
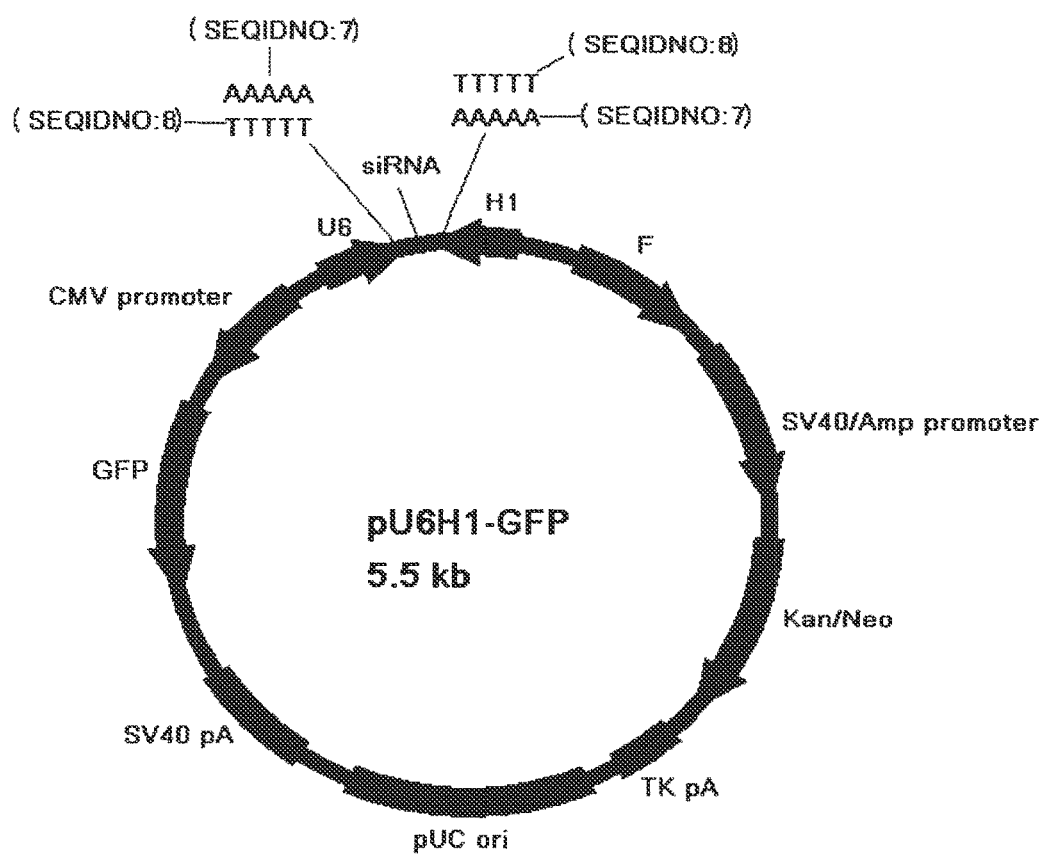
FIG. 2 Schematic Diagram of an siRNA Expression Vector (pU6H1-GFP) Map and MCS Sequences Before and After Cloning.

7.) Cloning into an siRNA Expression Vector:

After a gel purification, the FokI digested products can be cloned into a pre-prepared siRNA expression vector with over $T_4$ hands at both 3' ends (dephosphorylated), flanked by two tandem RNA polymerase III promoters such as U6 and H1 (FIG. 2). Poly(A/T)$_5$ act as the initial and termination signals for RNA polymerase III promoters as described previously. After *E. coil* transformation, the resulting siRNA polynucleotide pool has a size distribution same as that the Loop-1 linkers restricted (e.g., 19-2.3 bp).

EXAMPLE 1

Oligo Sequences and Preparation (A) Loop Phosphate Linkers: (Synthesized by Sigma-Aldrich) Loop-1 Linker(s):

19LP:

```
                                        (SEQ ID NO: 25)
5'CTTTTTTTCTGCTG CATCCCTGAACTGGGATCCGTTGGATGTGT
3'GAAAAAAAGACGAC GTAGGGACTTGACCCTAGGCAACCTACACA
                    (SEQ ID NO: 26)
       EcoP15I  FokI
```

20LP:
    -1T         +1G
```
                                        (SEQ ID NO: 27)
5'CTTTTTTCTGCTGGCATCCCTGAACTGGGATCCGTTGGATGTGT
3'GAAAAAAGACGACCGTAGGGACTTGACCCTAGGCAACCTACACAACA
       EcoP15I  FokI     (SEQ ID NO: 28)
```

21LP:
    -2T         +2G
```
                                        (SEQ ID NO: 29)
5'CTTTTTCTGCTGGGCATCCCTGAACTGGGATCCGTTGGATGTGT
3'GAAAAAGACGACCCGTAGGGACTTGACCCTAGGCAACCTACACA
       EcoP15I  FokI     (SEQ ID NO: 30)
```

22LP:
    -3T         +3G
```
                                        (SEQ ID NO: 31)
5'CTTTTCTGCTGGGGCATCCCTGAACTGGGATCCGTTGGATGTGT
3'GAAAAGACGACCCCGTAGGGACTTGACCCTAGGCAACCTACACA
       EcoP15I  FokI     (SEQ ID NO: 32)
```

23LP:
    -1C;  -3T    +4G
```
                                        (SEQ ID NO: 33)
5'TTTTCTGCTGGGGCATCCCTGAACTGGGATCCGTTGGATGTGT
3'AAAAGACGACCCCGTAGGGACTTGACCCTAGGCAACCTACACA
       EcoP15I  FokI     (SEQ ID NO: 34)
```

Loop linker-2:
```
                                        (SEQ ID NO: 35)
5'CTTTTTGAGACCGACATCCCTCTGCAGACGATCCATCAGAGTCAG
3'GAAAAACTCTGGCTGTAGGGAGACGTCTGCTAGGTAGTCTCAGTC
       FokI     (SEQ ID NO: 36)
```

Each (100 mM) phosphate linker listed above was denatured at 95° C. in a PCR thermocycler for 1 minute (min) and then self annealed to a loop by cooling down to room temperature. After gel purification, each looped linker was diluted with 1.times.TE buffer to 50 mM and stored at −70° C. until use.

(B) PCR Primers (the Following PCR Primers Synthesized by Invitrogen)

```
PCR-1 primer:
BH1:
                            (SEQ ID NO: 37)
5' ACACATCCA ACGGATCCCAGTTCAG 3'

PCR-2 primers:
BH1:
                            (SEQ ID NO: 38)
5' ACACATCCA ACGGATCCCAGTTCAG 3'

LG:
                            (SEQ ID NO: 39)
5' GACTCTGATGGATCGTCTGCAGAG 3'
```

(C) PCP Quaility Control Primers:

```
                                        (SEQ ID NO: 40)
    5' U6: 5' AAGGTCGGGCAGGAAGAGGGC 3'

(SEQ ID NO: 41)
    3' H1: 5' TATTTGCATGTCGCTATGTGTTCT 3'
```

Each one was diluted with 1.times.TE buffer to 10 mM and stored at −70° C. until use.

EXAMPLE 2

DNA Partial Digestion by DNaseI (1) Starting DNA: SARS coronavirus membrane protein (NCBI accession No.: AY536759) full-length cDNA (666 bp).

(2) One μg of SARS coronavirus membrane protein full-length cDNA was partially digested into 100-300 bp blunt-end fragments by DNaseI (Roche Biosystem; 0.01~0.03 U) in a $Mn^{2+}$ buffer at a final concentration of 10 mM Tris-HCl (pH9.0); 2 mM $MgSO_4$; 10 mM KCl; 8 mM $(NH_4)_2SO_4$ and 1 mM $MnCl_2$. The reaction was performed on ice for 1 min following by heating inactivation for 20 min at 70° C. The resulting products were analyzed on 1% Agarose gel.

EXAMPLE 3

Loop-1 Linkers Ligation and PCR-1 Amplification

Loop-1 Linkers Ligation

The partially digested products were ligated to Loop-1 phosphate linker(s) (19-; 20-; 21-; 22- and 23-bp Loop-1 linker) respectively. 5 L of ligation reaction mix contained: 2.5 μL partially digested DNA; 0.5 μL 10×ligation reaction buffer (500 mM Tris-HCl (pH 7.5, 25° C.), 100 mM $MgCl_2$, 100 mM dithiothreitol (DTT), 25 μg/μL bovine serum albumin (BSA); 1 μl (10 mM) Loop-1 linker; 0.5 μL 10 mM ATP, 0.5 μl T4 DNA Ligase (NEB). The reaction was performed at 16° C. overnight.

PCR-1 Amplification

The reaction mixture (50 μl) contained: 0.5 μl each Loop-1 ligated product; 2 μL single primer BH1 (20 μM), 1 μl dNTP (10 mM), 5 μl 10×PCR buffer (200 mM Tris-HCl (pH 8.4), 500 mM KCl, 15 mM $MgCl_2$), 0.5 μl Taq DNA polymerase and 41 μL PCR $H_2O$. The thermal cycling was as follows: preheating at 95° C. for 1 min; 28 cycles of 95° C. for 15 s; 68° C. for 1 min. Three μL of each PCR products were analyzed on a 1% Agarose gel.

EXAMPLE 4

EcoP15I Cleavage, Blunt-Ending and PAGE Purification

EcoP15I Cleavage

5 μL of each PCR-1 products generated by five (19-; 20-; 21-; 22- and 23 bp) Loop-1 linkers were mixed. An EcoP15I digestion solution (100 μL) contained: 10 μL PCR-1 product mixture, 10 μL ATP (10 mM), 10 μL 10×NEBuffer-3, 1 μL BSA (100×; 10 mg/mL), 10 μl (100 U) EcoP15I (NEB), 59 μL D-$H_2O$ and then placed in a 37° C. water bath for an overnight incubation.

Blunt-Ending

After phenol-chloroform extraction and ethanol precipitation, the pellet was dissolved with 11 μL D-$H_2O$, add 1.5 μL (4.5 U) T4 polymerase (NEB), 1.5 μL NEB Buffer-2 and 2 μL dNTP (1 mM) to a total 15 μL reaction volume and incubated at 37° C. for 15 min in a PCR thermal cycler. The reaction was inactivated by heating at 68° C. for 20 min.

PAGE Purification 1.5 μl DNA Loading Buffer (30 mM EDTA; 36% (V/V) glycerol; 0.05% (W/V) BPB, pH=7.0) was added into the 15 μL reaction and the reaction product was loaded onto a polyacrylamide gel 6.5 μL/well for 20% TBE polyacrylamide gel Electrophoresis (at 200V for 90 min). The specific 66 bp DNA fragments were observed after 10% EtBr staining (20 min) under a UV lamp. The gel was cut into pieces containing 66 bp fragments, and put together in a fresh tube containing 150 μL gel diffusion buffer (0.5M $NH_4AC$, 10 mM $Mg(Ac)_2$, 1 mM EDTA; pH 8.0). The tube was incubated at 55° C. overnight. DNA was extracted with QIAEX II Gel Extraction Kit and elute DNA with D-$H_2O$.

EXAMPLE 5

Loop-2 Linker Ligation and PCR-2 Amplification

Loop-2 Linker Ligation

Five .mu.L ligation reaction contained: 2.5 μL DNA isolated by PAGE, 0.5 μL 10×ligation reaction buffer (500 mM Tris-HCl (pH 7.5, 25° C.), 100 mM $MgCl_2$, 100 mM DTT, 25 μg/mL BSA), 1 μL (20 mM) Loop-2 linker, 0.5 μL ATP (10 mM), 0.5 μL T4 DNA Ligase (NEB) and 0.5 μL D-$H_2O$. The ligation reaction was incubated the reaction at 16° C. overnight in a PCR thermal cycler.

PCR-2 Amplification

The 5 μL ligation-2 product was diluted with 45 μL D-$H_2O$ and take out 0.5 μL as a template for PCR-2 amplification. A 50 μL reaction contained: 0.5 μL diluted ligation-2 template, 5 μL 10×PCR buffer (200 mM Tris-HCl (pH 8.4), 500 mM KCl, 15 mM $MgCl_2$), 1 μL LG primer (10 μM), 1 μL BH1(10 μM), 1 μL dNTP (10 mM), 0.5 μL Taq DNA polymerase, 41 μL PCR $H_2O$. The thermal cycling was as follows: preheating at 95° C. for 1 min; 28 cycles of 95° C. for 15 s; 68° C. for 1 min. After amplification, 10 μL PCR product was analyzed on a 20% TBE polyacrylamide gel. A specific 109 bp amplicon was observed after 10% EtBr staining (20 min) under a UV lamp, After phenol: chloroform extraction, the ethanol precipitation was performed at −20° C. at least for 2 hours. Pellet The DNA was centrifuged and the resultant DNA pellet was dissolved in 20 μL D-$H_2O$.

EXAMPLE 6

FokI Digestion

A 100 μL reaction contained: 20 μL above PCR-2 product, 2 μL FokI (8 U; NEB), 10 μL NEBuffer-3 and 72 μL D-$H_2O$, which was incubated at 37° C. for 2 hrs. After the digestion reaction 10 μL of the Fok1 digested DNA was analyzed on a 20% TBE polyacrylamide gel. The target bands were distributed from 29 to 33 bp in length, which corresponds to siRNA having 19-23 bp having 10 bp cloning sites ("AAAAG" (SEQ ID NO:41) at both 5' ends). Three other 3 bands from top to bottom were: an undigested 109 bp band, a partial digested band (siRNA with a loop at one side), a Loop-1 and Loop-2 overlapping band (owing to Loop-1 and Loop-2 overlap each other, the signal is strong).

EXAMPLE 7

Vector Ligation and Completion of siRNA Library

Ligation into an siRNA Expression Vector

DNA fragments after FokI digestion were ligated into an siRNA expression vector: pU6H1-GFP (NT Omics, USA) with double promoters of U6 and H1 (FIG. 2). A 15 μL ligation mixture contained: 1 μL (100 ng) pU6H1-GFP, 2 μL FokI digested DNA, 10 μL 1.5×Plasmid Ligation Buffer (90 mM Tris (PH8.5-9.0); 12 mM DTT; 60 mM MgCl$_2$; 40% PEG8000), 0.5 μL ATP (10 mM), 0.25 μL T4 DNA Ligase (NEB), 2.25 μl D-H$_2$O. The reaction was incubated at 16° C. for 30 min. 85 μL D-H$_2$O was added to the ligation mixture and ethanol-precipitated an ethanol precipitated at −70° C. for 30 minutes. The precipitated DNA was centrifuged forming a DNA pellet and the pellet was dissolved in 5 μL D-H$_2$O.

Electrotransformation

Electro-competent cells, MegaX DH10B.TM. (Invitrogen) were thawed on ice, 5 μL ligation product was mixed in 40 μL electro-competent cells and placed in ice for 1 min. The mixture was transferred into a cuvette (BioRad) to perform electrotransformation in a MicroPulser (BioRad). After transformation the mixture was transferred to a fresh tube containing 150 μL SOC medium (2% (W/V)) Tryptone, 0.5% (W/V) Yeast, 0.05% (W/V) NaCl, 2.5 mM KCl, 11 mM MgCl$_2$, 20 mM glucose, pH=7.0) and incubated was performed at 37° C. with a continuous shaking for 40~60 min at 220 rpm, followed by plating the bacterial culture on a solid medium (1% (W/V) Tryptone, 0.5% (W/V) NaCl, 1.5% (W/V) Agar, pH=7.0; 50 μg/mL Kanamycine), which was incubated at 37° C. in an air incubator overnight. One ligation reached 1×10$^3$ independent clones (colonies).

EXAMPLE 8 siRNA Library Validation

Sample Inoculation

The well-isolated colonies were randomly picked and inoculated into separate 1.5 mL eppendorf tube (or 48-well plate), each containing 400 μL LB medium (1% (WV) Tryptone, 0.5% (W/V) Yeast, 1% (W/V) NaCl, pH=7.0). Incubation was performed at 37° C. with a continuous shaking for 2 hours at 220 rpm.

PCR-Based Insert Screening

The reaction mixture (30 HL) contained: 2 μL above bacteria culture, 0.5 μL 5' U6 primer (10 μM), 0.5 μL 5' H1 primer (10 μM), 0.5 μl dNTP (10 mM), 3 L 10×PCR buffer (200 mM Tris-HCl (pH 8.4), 500 mM KCl, 15 mM MgCl$_2$), 0.3 μL Taq DNA polymerase and 23.2 μL PCR H$_2$O. The thermal cycling was as follows: preheating at 95° C. for 5 min; 25 cycles of 95° C. for 15 s; 62° C. for 30 s; 72° C. for 40 s; holding at 72° C. for 7 min for last extension. Five μL of each PCR products were analyzed on 1% Agarose gel, The positive bands of PCR products were ~400 bp in length. The positive rate for sampling was 91.6% (44/48).

SfiI Digestion of PCR Products

The size of the siRNAs ranged from 19-23 bp in length. To further validate siRNA positive clones, SfiI restriction enzyme was added to PCR products. The SfiI restriction site was originally in the MCS (multiple cloning sites) region of pU6H1-GFP vector used. A positive digestion indicates siRNA insert negative ((just a vacant vector). The SfiI digestion mixture contained: 4 μL above PCR products, 0.25 μL (5 U) SfiI (NEB), 0.75 μL NEBuffer-2. Digestion was incubated at 50° C. for 1.5 hr in a PCR thermal cycler. Five μL SfiI digestion mixture was analyzed on 1% Agarose gel. Out of the 43 testing samples, only 1 could be digested by SfiI, indicating that the recombination rate of the experimental SARS siRNA library was 97.6% (43/44).

Plasmid Mini Preparation and Sequencing

100 μL of bacteria culture was inoculated with PCR/SfiI positive constructs into a culture tube containing 4 mL LB medium (1% (W/V) Tryptone, 0.5% (W/V) Yeast, 1% (W/V) NaCl, pH=7.0; 50 μL/mL Kanamycine). An overnight incubation was performed at 37° C. with a continuous shaking for 2 hours at 220 rpm. 3.2 mL of it was taken for mini sale plasmid extraction with TIAN Prep Mini plasmid Kit ((TIANGEN), store the remaining in 20% glycerol at −20° C. for further use. One μL (150~200 ng) purified plasmid of each sample was analyzed on 1% Agarose gel. The plasmids were sequenced (Shanghai Invitrogen) and the resultant iNA sequences were aligned with the SARS full-length cDNA sequence by an alignment program software. The results are listed in TABLE I. The length of siRNA clones is distributed from 19 to 23 bp with a random binding sites distribution. The results confirm that the experimental SRAR siRNA library is representative both in length and binding sites.

TABLE 1

Sequencing Results for Clones Selected from the Experimental SARS siRNA Library

| NO. | Clone NO. | siRNA sequences | Length (bp) | Sites (nt) |
|---|---|---|---|---|
| 1 | S061218-1 | TACAATTTGCCTATTCTAATC (SEQ ID NO: 43) | 21 | 101~121 |
| 2 | S061218-11 | GGCTCTTGTGGCCAGTAACA (SEQ ID NO: 44) | 20 | 161~181 |
| 3 | S061220-10 | GGAAAACAAGCTTTATTATG (SEQ ID NO: 45) | 20 | 529~510 |
| 4 | S061220-19 | TACGGTAGCGGTTGTATGC (SEQ ID NO: 46) | 19 | 87~69 |
| 5 | S070115-21 | TATTCTAATCGGAACAGGTT (SEQ ID NO: 47) | 20 | 112~131 |
| 6 | S070115-26 | GAGCAAACAGCCTGAAGGAAGC (SEQ ID NO: 48) | 22 | 378~357 |
| 7 | S070115-46 | GTACCCGCTCAATGTGGTCA (SEQ ID NO: 49) | 20 | 311~330 |

TABLE 1-continued

Sequencing Results for Clones Selected from the
Experimental SARS siRNA Library

| NO. | Clone NO. | siRNA sequences | Length (bp) | Sites (nt) |
|---|---|---|---|---|
| 8 | S070119-27 | GTACATAATAAAGCTTGTTTTCC (SEQ ID NO: 50) | 23 | 135~157 |
| 9 | S070119-28 | AGAATGTTTGTTTCTGGGT (SEQ ID NO: 51) | 19 | 332~312 |
| 10 | S070119-30 | CATTGGTGCTGTGATCATTC (SEQ ID NO: 52) | 20 | 414~433 |
| 11 | S070119-31 | GAGAATGTTTGTTTCTGGGT (SEQ ID NO: 53) | 20 | 332~314 |
| 12 | S070119-32 | CTTTATTATGTACAAAAACC (SEQ ID NO: 54) | 20 | 539~520* |
| 13 | S070119-34 | GATTAGAATAGGCAAATTGT (SEQ ID NO: 55) | 20 | 565~546 |
| 14 | S070122-7 | GGAAGCAACGAAGTAGCTAAGCC (SEQ ID NO: 56) | 23 | 395~373 |
| 15 | S070122-12 | GAGCGGGTACGAGCAAACAGCC (SEQ ID NO: 57) | 22 | 368~347 |
| 16 | S070122-14 | TCTCCGGGGACAATTGTGAC (SEQ ID NO: 58) | 21 | 366~386* |
| 17 | S070122-19 | TGTTACTACAATTTGCCTATTC (SEQ ID NO: 59) | 22 | 95~116 |
| 18 | S070122-22 | GCTTTATTATGTACAAAAACC (SEQ ID NO: 60) | 21 | 539~519* |
| 19 | S070122-30 | GAATGACCACATTGAGCGGGT (SEQ ID NO: 61) | 21 | 354~334 |
| 20 | S070122-32 | GTGATGTAGCCACAGTGATC (SEQ ID NO: 62) | 20 | 169~150 |
| 21 | S070122-48 | TCAACCCAGAAACAAAGATTC (SEQ ID NO: 63) | 21 | 332~352 |
| 22 | S070307-4 | GTATTGTAGGCTTGATGTGGCT (SEQ ID NO: 64) | 22 | 254~275* |
| 23 | S070307-45 | CTACAATTTGCCTATTCTAATC (SEQ ID NO: 65) | 22 | 100~121 |
| 24 | S070307-48 | TACAATACAAGCCATTGCAATC (SEQ ID NO: 66) | 22 | 427~406 |
| 25 | S070316-11 | CATCAAGCCTACAATACAAGCC (SEQ ID NO: 67) | 22 | 418~397* |

(*Repeated clones)

I claim:

1. A DNA duplex comprising a sense strand and an antisense strand, wherein the sense strand comprises a first flanking segment, a middle segment, and a second flanking segment, and the antisense strand comprises a first flanking segment, a middle segment, and a second flanking segment, wherein:
   each strand and segment independently has a 5' end and a 3' end;
   the 3' end of the first flanking segment of the sense strand and the 5' end of the middle segment of the sense strand are ligated;
   the 3' end of the middle segment of the sense strand and the 5' end of the second flanking segment of the sense strand are ligated;
   the 3' end of the first flanking segment of the antisense strand and the 5' end of the middle segment of the antisense strand are ligated;
   the 3' end of the middle segment of the antisense strand and the 5' end of the second flanking segment of the antisense strand are ligated;
   the middle segment of the sense strand and the middle segment of the antisense strand are complementary and form a duplex that comprises 100-300 base pairs;
   the first flanking segment of the sense strand and the second flanking segment of the antisense strand are complementary and form a duplex that comprises:
   (a) a first type III restriction enzyme recognition site,
   (b) a first poly-A sequence in the sense strand having at least four deoxyadenosine (A) nucleotides, wherein the first poly-A sequence is disposed between the first type III restriction enzyme recognition site and the 5' end of the middle segment of the sense strand, and is directly linked to the first type III restriction enzyme recognition site, and
   (c) a first type II restriction enzyme recognition site nucleotide sequence in the first flanking segment of the sense strand, wherein the first type III restriction enzyme recognition site is disposed between the first type II restriction enzyme recognition site and the first poly-A sequence;
   the second flanking segment of the sense strand and the first flanking segment of the antisense strand are complementary and form a duplex that comprises:
   (a) a second type III restriction enzyme recognition site,
   (b) a second poly-A sequence in the antisense strand having at least four deoxyadenosine nucleotides, wherein the second poly-A sequence is disposed between the second type III restriction enzyme recognition site and the 5' end of the middle segment of the antisense strand, and is directly linked to the second type III restriction enzyme recognition site and
   (c) a second type II restriction enzyme recognition site nucleotide sequence in the first flanking segment of the antisense strand, wherein the second type III restriction enzyme recognition site is disposed between the second type II restriction enzyme recognition site and the second poly-A sequence; and
   the first type III restriction enzyme recognition site and the second type III restriction enzyme recognition site are inversely oriented and configured head to head.

2. The DNA duplex of claim 1, wherein the first and second type III restriction enzyme recognition sites are each EcoP15I or EcoP15 recognition sites.

3. The DNA duplex of claim 1, wherein the first and second poly-A sequences each consist of 4, 5, 6, or 7 deoxyadenosine nucleotides.

4. The DNA duplex of claim 3, further comprising: (a) a deoxyguanosine nucleotide disposed between the first poly-A sequence and the 5' end of the middle segment of the sense strand, and (b) a deoxyguanosine nucleotide disposed between the second poly-A sequence and the 5' end of the middle segment of the antisense strand.

5. The DNA duplex of claim 1, wherein the first and second type II restriction enzyme recognition sites are each FokI recognition sites.

6. The DNA duplex of claim 5, wherein the first and second type III restriction enzyme recognition sites are each EcoP15I or EcoP15 recognition sites.

7. The DNA duplex of claim 1, further comprising:
   (a) 0, 1, 2, 3, or 4 base pairs disposed between the first type II restriction enzyme recognition site and the first type III restriction enzyme recognition site; and
   (b) 0, 1, 2, 3, or 4 base pairs disposed between the second type II restriction enzyme recognition site and the second type III restriction enzyme recognition site.

8. The DNA duplex of claim 7, wherein:
(a) the first flanking segment of the sense strand comprises:
   (i) the first poly-A sequence consisting of $X_1$ deoxyadenosine nucleotides, wherein $X_1$ is 4, 5, 6, or 7;
   (ii) $Y_1$ deoxyguanosine nucleotides disposed between the first poly-A sequence and the 5' end of the middle segment, wherein $Y_1$ is 0 or 1; and
   (iii) $Z_1$ base pairs disposed between the first type II restriction enzyme recognition site and the first type III restriction enzyme recognition site, wherein $Z_1$ is 0, 1, 2, 3, or 4; and
wherein $X_1+Y_1+Z_1=8$; and
(b) the first flanking segment of the antisense strand comprises:
   (i) the second poly-A sequence consisting of $X_2$ deoxyadenosine nucleotides, wherein $X_2$ is 4, 5, 6, or 7;

(ii) $Y_2$ deoxyguanosine nucleotides disposed between the first poly-A sequence and the 5' end of the middle segment, wherein $Y_2$ is 0 or 1; and (iii) $Z_2$ base pairs disposed between the second type II restriction enzyme recognition site and the second type III restriction enzyme recognition site, wherein $Z_2$ is 0, 1, 2, 3, or 4; and wherein $X_2+Y_2+Z_2=8$.

9. The DNA duplex of claim 1, having two ends, wherein each end comprises a hairpin loop.

10. The DNA duplex of claim 9, wherein each hairpin loop comprises a duplex stem of 25 base pairs, and each of: the first or second type III restriction enzyme recognition sites, the first or second poly-A sequences, and the first or second type II restriction enzyme recognition sites of the DNA duplex are located outside of the duplex stem of the hairpin loop.

11. A DNA duplex comprising a sense strand and an antisense strand, wherein the sense strand comprises a first flanking segment, a middle segment, and a second flanking segment, and the antisense strand comprises a first flanking segment, a middle segment, and a second flanking segment, wherein:

each strand and segment independently has a 5' end and a 3' end;

the 3' end of the first flanking segment of the sense strand and the 5' end of the middle segment of the sense strand are ligated;

the 3' end of the middle segment of the sense strand and the 5' end of the second flanking segment of the sense strand are ligated;

the 3' end of the first flanking segment of the antisense strand and the 5' end of the middle segment of the antisense strand are ligated;

the 3' end of the middle segment of the antisense strand and the 5' end of the second flanking segment of the antisense strand are ligated; and wherein:

(a) the middle segment of the sense strand and the middle segment of the antisense strand are complementary and form a duplex that comprises 100-300 base pairs;

(b) the first flanking segment of the sense strand and the second flanking segment of the antisense strand are complementary and form a duplex that comprises:

(i) a first FokI recognition site;

(ii) a first EcoP15I or EcoP15 recognition site; and (iii) a first poly-A sequence in the sense strand having $X_1$ nucleotides, wherein $X_1$ is 4, 5, 6, or 7;

wherein the first EcoP15I or EcoP15 recognition site is disposed between the first FokI recognition site and the first poly-A sequence, and the first poly-A sequence is disposed between the first EcoP15I or EcoP15 recognition site and 5' end of the middle segment of the sense strand, and is directly linked to the first EcoP15I or EcoP15 recognition site, (iv) $Y_1$ deoxyguanosine nucleotides disposed between the first poly-A sequence and the 5' end of the middle segment of the sense strand, wherein $Y_1$ is 0 or 1, (v) $Z_1$ base pairs disposed between the first FokI recognition site and the first EcoP15I or EcoP15 recognition site, wherein X1+Y1+Z1=8; and (c) the second flanking segment of the sense strand and the first flanking segment of the antisense strand are complementary and form a duplex that comprises:

(i) a second FokI recognition site;

(ii) a second EcoP15I or EcoP15 recognition site; and (iii) a second poly-A sequence in the antisense strand having $X_2$ nucleotides, wherein $X_2$ is 4, 5, 6, or 7;

wherein the second EcoP15I or EcoP15 recognition site is disposed between the second FokI recognition site and the second poly-A sequence, and the second poly-A sequence is disposed between the second EcoP15I or EcoP15 recognition site and the 5' end of the middle segment of the antisense strand, and is directly linked to the second EcoP15I or EcoP15 recognition site ; and (iv) $Y_2$ deoxyguanosine nucleotides disposed between the first poly-A sequence and the 5' end of the middle segment of the antisense strand, wherein $Y_2$ is 0 or 1, (v) $Z_2$ base pairs disposed between the second FokI recognition site and the second EcoP15I or EcoP15 recognition site, wherein $X_2+Y_2+Z_2=8$.

12. The DNA duplex of claim 1, wherein:
the first flanking segment of the sense strand comprises SEQ ID NO:80 and the second flanking segment of the antisense strand comprises SEQ ID NO:79;
the first flanking segment of the sense strand comprises SEQ ID NO:72 and the second flanking segment of the antisense strand comprises SEQ ID NO:71;
the first flanking segment of the sense strand comprises SEQ ID NO:74 and the second flanking segment of the antisense strand comprises SEQ ID NO:73;

the first flanking segment of the sense strand comprises SEQ ID NO:76 and the second flanking segment of the antisense strand comprises SEQ ID NO:75; or the first flanking segment of the sense strand comprises SEQ ID NO:78 and the second flanking segment of the antisense strand comprises SEQ ID NO:77.

13. The DNA duplex of claim 1, wherein:
the first flanking segment of the sense strand comprises SEQ ID NO:26 and the second flanking segment of the antisense strand comprises SEQ ID NO:25;
the first flanking segment of the sense strand comprises SEQ ID NO:28 and the second flanking segment of the antisense strand comprises SEQ ID NO:27;
the first flanking segment of the sense strand comprises SEQ ID NO:30 and the second flanking segment of the antisense strand comprises SEQ ID NO:29;

the first flanking segment of the sense strand comprises SEQ ID NO:32 and the second flanking segment of the antisense strand comprises SEQ ID NO:31; or the first flanking segment of the sense strand comprises SEQ ID NO:34 and the second flanking segment of the antisense strand comprises SEQ ID NO:33.

14. The DNA duplex of claim 13, wherein the middle segment of the sense strand and the middle segment of the antisense strand are complementary and form a duplex that comprises 100-300 base pairs derived from a full-length cDNA of a SARS coronavirus membrane protein.

15. The DNA duplex of claim 1, wherein the middle segment of the sense strand and the middle segment of the antisense strand are complementary and form a duplex that comprises 100-300 base pairs derived from a full-length cDNA of a SARS coronavirus membrane protein.

16. The DNA duplex of claim 1, wherein the first and second type III restriction enzyme recognition sites are identical, and the first and second type II restriction enzyme recognition sites are identical.

* * * * *